US008753873B2

(12) United States Patent
Luckey

(10) Patent No.: US 8,753,873 B2
(45) Date of Patent: Jun. 17, 2014

(54) MULTIPLEXED MICROARRAY ASSEMBLY AND METHOD FOR FABRICATING A MULTIPLEXED MICROARRAY

(75) Inventor: John A. Luckey, Merrimac, WI (US)

(73) Assignee: Roche NimbleGen, Inc., Madison, WI (US)

( * ) Notice: Subject to any disclaimer, the term of this patent is extended or adjusted under 35 U.S.C. 154(b) by 25 days.

(21) Appl. No.: 13/397,061

(22) Filed: Feb. 15, 2012

(65) Prior Publication Data

US 2012/0264650 A1 Oct. 18, 2012

Related U.S. Application Data

(60) Provisional application No. 61/476,112, filed on Apr. 15, 2011.

(51) Int. Cl.

| | |
|---|---|
| ***C12M 1/34*** | (2006.01) |
| ***C12M 3/00*** | (2006.01) |
| ***C12M 1/00*** | (2006.01) |
| ***G01N 15/06*** | (2006.01) |
| ***G01N 33/00*** | (2006.01) |
| ***G01N 33/48*** | (2006.01) |

(52) U.S. Cl.

USPC ...... 435/287.1; 435/283.1; 422/50; 422/68.1; 422/417

(58) Field of Classification Search

USPC .................. 435/6.1, 6.11, 91.1, 283.1, 287.1, 435/287.2; 436/94, 501; 536/23.1, 24.3; 422/50, 68.1, 417

See application file for complete search history.

(56) References Cited

U.S. PATENT DOCUMENTS

| | | | | |
|---|---|---|---|---|
| 5,545,531 | A | 8/1996 | Rava et al. | |
| 5,796,039 | A * | 8/1998 | Daoud | 174/59 |
| 5,874,219 | A | 2/1999 | Rava et al. | |
| 6,309,824 | B1 | 10/2001 | Drmanac | |
| 6,548,020 | B2 | 4/2003 | Okamoto et al. | |
| 6,594,432 | B2 | 7/2003 | Chen et al. | |
| 6,703,203 | B2 | 3/2004 | Shao et al. | |
| 6,916,621 | B2 | 7/2005 | Shah | |
| 6,998,236 | B2 | 2/2006 | Shao et al. | |
| 7,335,470 | B2 | 2/2008 | Mohammed et al. | |
| 7,349,346 | B2 | 3/2008 | Castelino | |
| 7,358,097 | B2 | 4/2008 | Seul et al. | |

(Continued)

FOREIGN PATENT DOCUMENTS

| | | |
|---|---|---|
| CN | 1137999 C | 2/2004 |
| EP | 0895083 A2 | 2/1999 |

(Continued)

OTHER PUBLICATIONS

European Search Report for Application No. 12164024.7-2113/2511009, dated Nov. 27, 2012, 7 pages.

*Primary Examiner* — Frank Lu

(74) *Attorney, Agent, or Firm* — Barnes & Thornburg LLP

(57) ABSTRACT

Multiplexed microarrays, multiplexed microarray cassettes, and methods for fabricating multiplexed microarrays are disclosed. In some embodiments, the multiplexed microarrays include a substrate, a chamber layer, and at least one channel layer. The topmost channel layer forms a port layer and may be compressible. The multiplexed microarrays may also include a compressible or non-compressible cover or sealing film. The multiplexed microarray cassette includes a base and may also include a cover. The base of the multiplexed microarray cassette includes a plurality of tracks to receive corresponding multiplexed microarrays.

31 Claims, 19 Drawing Sheets

(56) References Cited

U.S. PATENT DOCUMENTS

| | | | | |
|---|---|---|---|---|
| 7,425,311 | B2 | 9/2008 | Gfrorer et al. | |
| 2002/0048765 | A1 | 4/2002 | Shao et al. | |
| 2002/0144738 | A1 * | 10/2002 | Unger et al. | 137/824 |
| 2002/0187560 | A1 * | 12/2002 | Pezzuto et al. | 436/180 |
| 2003/0026739 | A1 | 2/2003 | MacBeth et al. | |
| 2004/0071605 | A1 | 4/2004 | Coonan et al. | |
| 2004/0101949 | A1 | 5/2004 | Green et al. | |
| 2004/0110211 | A1 | 6/2004 | McCormick et al. | |
| 2004/0208792 | A1 | 10/2004 | Linton et al. | |
| 2005/0014184 | A1 | 1/2005 | Shah | |
| 2005/0136459 | A1 | 6/2005 | Lee et al. | |
| 2005/0282156 | A1 | 12/2005 | Rava et al. | |
| 2006/0057580 | A1 | 3/2006 | Zou et al. | |
| 2007/0238870 | A1 | 10/2007 | Kawase et al. | |
| 2009/0042734 | A1 | 2/2009 | Yoshida et al. | |

FOREIGN PATENT DOCUMENTS

| | | | |
|---|---|---|---|
| EP | 0907889 | A1 | 4/1999 |
| EP | 1299564 | A2 | 4/2003 |
| EP | 1371980 | A2 | 12/2003 |
| EP | 1415715 | A1 | 5/2004 |
| EP | 1544655 | A2 | 6/2005 |
| EP | 1835019 | A1 | 9/2007 |
| EP | 1870709 | A1 | 12/2007 |

* cited by examiner

MULTIPLEXED MICROARRAY ASSEMBLY AND METHOD FOR FABRICATING A MULTIPLEXED MICROARRAY

CROSS-REFERENCE TO RELATED U.S. PATENT APPLICATION

The present application claims priority under 35 U.S.C. §119(e) to U.S. Provisional Patent Application Ser. No. 61/476,112, entitled "MULTIPLEXED MICROARRAY ASSEMBLY AND METHOD FOR FABRICATING A MULTIPLEXED MICROARRY" by John A. Luckey, which was filed on Apr. 15, 2011, the entirety of which is hereby incorporated by reference.

TECHNICAL FIELD

The present disclosure relates, generally, to microarrays and, more particularly, to multiplexed microarrays for performing multiple assays and other tests or experiments.

BACKGROUND

Deoxyribonucleic acid (DNA) microarray technology is used in many research areas such as gene expression and discovery, mutation detection, allelic and evolutionary sequence comparison, genome mapping, and the like. Microarrays allow researchers to perform a large number of concurrent experiments using, for example, multiple probes and a single test sample. In typical microarrays, the microarray area is surrounded by a barrier such that the test sample may be placed in contact with the microarray but restricted from flowing out of the defined microarray area.

Multiplexed microarrays are formed from multiple microarrays positioned on a single substrate. In a multiplexed microarray, a barrier may be used to surround each individual microarray such that a plurality of samples may be used with a single multiplexed microarray. The barrier retains the sample within the desired sub-array while restricting the sample from flowing or otherwise contacting adjacent or nearby sub-arrays of the multiplexed microarray.

In some typical implementations, a pipette machine is utilized to deposit the samples to each sub-array of the multiplexed microarray. To facilitate proper application of the sample, each sub-array must be arranged in a predefined location usable by the pipette machine. However, depending on the type of microarray (e.g., synthesized arrays), the locations at which the microarrays may be formed on the substrate may not be directly compatible with the pipette machines thereby limiting the number of useful microarrays.

SUMMARY

According to one aspect, a multiplexed microarray includes a substrate, a chamber layer attached to the upper surface of the substrate, and a channel layer attached to an upper surface of the chamber layer. The substrate may include a plurality of microarrays formed on an upper surface of the substrate. The chamber layer may include a plurality of first apertures defined therethrough and the channel layer may include a plurality of second apertures defined therethrough. Each of the plurality of second apertures may be congruent with and superimposed over a corresponding first aperture of the chamber layer. In some embodiments, the first aperture, second aperture, and the upper surface of the substrate may cooperate to define a plurality of corresponding laterally elongated wells. Each elongated well may include a first lateral end at which a corresponding microarray of the plurality of microarrays is located and a second lateral end defining a fill port to receive an analyte such that the fill port is laterally offset from the corresponding microarray. The second lateral end may be fluidically coupled to the first lateral end to allow the analyte to contact the microarray.

In some embodiments, each microarray of the plurality of microarrays is spaced apart from an adjacent microarray a distance less than 9 millimeters. Additionally, each fill port is spaced apart from an adjacent fill port a distance of about 9 millimeters. In some embodiments, the substrate may include twenty-four microarrays formed on the upper surface of the substrate and each microarray may be spaced apart from an adjacent microarray a distance less than 9 millimeters. Additionally, the chamber layer may be formed from one of a hydrophobic plastic material and an elastomer material. In some embodiments, the channel layer is a compressible channel layer and may be formed from a polymer material. Additionally, in some embodiments, the multiplexed microarray may further include a coverplate. The coverplate may be coupled to an upper surface of the compressible channel layer. In such embodiments, the coverplate and compressible channel layer cooperate to pneumatically seal the plurality of elongated wells. In other embodiments, the coverplate may include a sealing gasket cooperating with the upper surface of the channel layer to pneumatically seal the plurality of elongated wells. Alternatively, in some embodiments, a sealing film may be coupled to an upper surface of the channel layer. The sealing film and the channel layer cooperating pneumatically seal the plurality of elongated wells. The coverplate may include a plurality of openings, which are superimposed over a corresponding fill port.

In some embodiments, the plan view, cross-sectional area of each elongated well is substantially equal. Additionally, in some embodiments, the plurality of laterally elongated wells may include a plurality of first elongated wells located toward a first longitudinal side of the multiplexed microarray and a plurality of second elongated wells located toward a second longitudinal side of the multiplexed microarray. The multiplexed microarray may also include a plurality of third elongated wells centrally located between the plurality of first elongated wells and second elongated wells, each of the third elongated wells having a corresponding microarray of the plurality of microarrays located therein.

According to another aspect, a method for fabricating a multiplexed microarray may include forming a plurality of microarrays on an upper surface of a substrate, attaching a chamber layer to the upper surface of the substrate such that each microarray of the plurality of microarrays is located in a corresponding aperture of a plurality of apertures defined through the chamber layer, and attaching a channel layer to an upper surface of the chamber layer such that each aperture of a plurality of second apertures defined through the channel layer is congruent with and superimposed over a corresponding first aperture of the physical barrier layer.

In some embodiments, the method may also include forming a plurality of elongated wells defined by the first aperture, second aperture, and the upper surface of the substrate. Each elongated well may have a first lateral end at which a corresponding microarray of the plurality of microarrays is located and a second lateral end defining a fill port to receive an analyte such that the fill port is laterally offset from the corresponding microarray. The second lateral end may be fluidically coupled to the first lateral end to allow the analyte to contact the microarray. The method may also include depositing an analyte into at least one of the fill ports.

Additionally, in some embodiments, the channel layer may be a compressible channel layer and the method may further include coupling a coverplate to an upper surface of the compressible channel layer subsequent to depositing the analyte. Additionally, the method may include coupling a coverplate including a sealing gasket to an upper surface of the channel layer subsequent to depositing the analyte. Alternatively, the method may include coupling a sealing film to an upper surface of the channel layer subsequent to depositing the analyte.

According to a further aspect, a multiplexed microarray may include a substrate, a chamber layer attached to the upper surface of the substrate, a first channel layer disposed on the chamber layer, and a port layer coupled to an upper surface of the first channel layer. The substrate may include a plurality of microarrays formed on an upper surface of the substrate. The chamber layer may include a plurality of apertures defined therethrough. The plurality of apertures and the upper surface of the substrate may cooperate to define a plurality of corresponding wells. Each well may include a corresponding one of the plurality of microarrays located therein. The first channel layer may include a plurality of first fluid channels. Each of the first fluid channels may be superimposed over a corresponding aperture of the chamber layer. The port layer may include a plurality of fill ports defined therethrough. Each fill port may be superimposed over a corresponding first fluid channel of the first channel layer such that each fill port is in fluid communication with a corresponding well through a corresponding first fluid channel.

In some embodiments, each fluid channel of the plurality of first fluid channels may be embodied as an elongated slit and an opening fluidically coupled to a lateral end of the elongated slit. The opening may include a first width greater than a second width of the elongated slit. In such embodiments, each fill port of the port layer is superimposed over a corresponding opening of a corresponding first fluid channel. Alternatively, each fluid channel of the plurality of first fluid channels may comprise a substantially circular opening and the first channel layer may further include a plurality of vent apertures and each fill port of the port layer may be superimposed over at least a portion of a corresponding vent aperture of the first channel layer.

In some embodiments, the multiplexed microarray may further include a second channel layer attached to the upper surface of the chamber layer. In some embodiments, the second channel layer may include a plurality of second fluid channels and a plurality of vent apertures. Each of the plurality of second fluid channels and the plurality of vent apertures may be superimposed over a corresponding well. In such embodiments, the first channel layer may be attached to an upper surface of the second channel layer such that each of the first channels are superimposed over a corresponding second fluid channel and at least a portion of each vent apertures of the first channel layer may be superimposed over a corresponding vent aperture of the second channel layer.

Alternatively, the second channel layer may include a plurality of second fluid channels. At least a portion of each second fluid channel may be superimposed over a corresponding well. In such embodiments, the first channel layer may be attached to an upper surface of the second channel layer such that each of the first channels are superimposed over a corresponding second fluid channel of the second channel layer. Additionally, in some embodiments, each fluid channel of the plurality of second channels comprises an elongated slit.

In some embodiments, the port layer may further include a plurality of vent holes. Each vent hole may be superimposed over at least one of the plurality of first channels of the first channel layer. Additionally, each microarray of the plurality of microarrays may be spaced apart from an adjacent microarray a distance less than 9 millimeters. Further, each fill port of the port layer may be spaced apart from an adjacent fill port a distance of about 9 millimeters. In some embodiments, the substrate may include twenty-four microarrays formed on the upper surface of the substrate. Each microarray may be spaced apart from an adjacent microarray a distance less than 9 millimeters. Additionally, in some embodiments, the plan view, cross-sectional area of each well may be substantially equal. Further, in some embodiments, the first channel layer may be compressible.

According to another aspect, a method for fabricating a multiplexed microarray may include forming a plurality of microarrays on an upper surface of a substrate, attaching a chamber layer to the upper surface of the substrate such that each microarray of the plurality of microarrays is located in a corresponding aperture of a plurality of apertures defined through the chamber layer, disposing a first channel layer on the chamber layer such that each of a plurality of first fluid channels of the first channel layer is superimposed over a corresponding aperture of the chamber layer, and coupling a port layer to an upper surface of the first channel layer such that each of a plurality of fill ports defined through the port layer is superimposed over a corresponding first fluid channel of the first channel layer.

In some embodiments, the method may also include attaching a second channel layer to an upper surface of the chamber layer such that each of a plurality of second fluid channels of the second channel layer is superimposed over a corresponding first aperture of the chamber layer. The method may additionally include attaching the first channel layer to an upper surface of the second channel layer such that each of first fluid channels is superimposed over and in fluid communication with a corresponding second fluid channel.

According to yet another embodiment, a multiplexed microarray cassette may include a base and a cover couplable to the base. The base may include a plurality of tracks to receive corresponding multiplexed microarrays. Each track may include a first lateral groove and a second lateral grove to receive a corresponding longitudinal side of a substrate of a corresponding multiplexed microarray. The base may also include a latch located at a longitudinal end of each track. Each latch may be movable from a first position to secure the corresponding multiplexed microarray in the corresponding track and a second position allowing the corresponding multiplexed microarray to be removed from the corresponding track. The base may also include a plurality of threaded apertures. The cover may include a plurality of track windows through which a corresponding multiplexed microarray is visible when received in the corresponding tracks of the base and the cover is coupled to the base. The base may also include a plurality of screws to be received in the threaded apertures to secure the cover to the base.

In some embodiments, the base may include four tracks to receive a corresponding four multiplexed microarrays. Additionally, in some embodiments, the base may include a first and second guide pin extending upwardly from a top surface of the base. In such embodiments, the cover includes a first and second aperture defined therethough and located to receive the corresponding first and second guide pin when the cover is secured to the base. Additionally, in some embodiments, the cover may include a lateral crossbar that divides each track window into a first window and a second window.

Additionally, in some embodiments, the cover may include a bottom surface that contacts an upper surface of the base when the cover is secured to the base. The bottom surface of the cover may include a plurality of recesses sized to receive a coverplate of a corresponding multiplexed microarray when the corresponding multiplexed microarray is received in a corresponding track of the base and the coverplate is coupled to the base. Additionally, the cover may include a screw located at a longitudinal end of each track window. Each screw may be adjustable to secure the corresponding multiplexed microarray in the corresponding recess of the cover.

DETAILED DESCRIPTION

Figure 1:
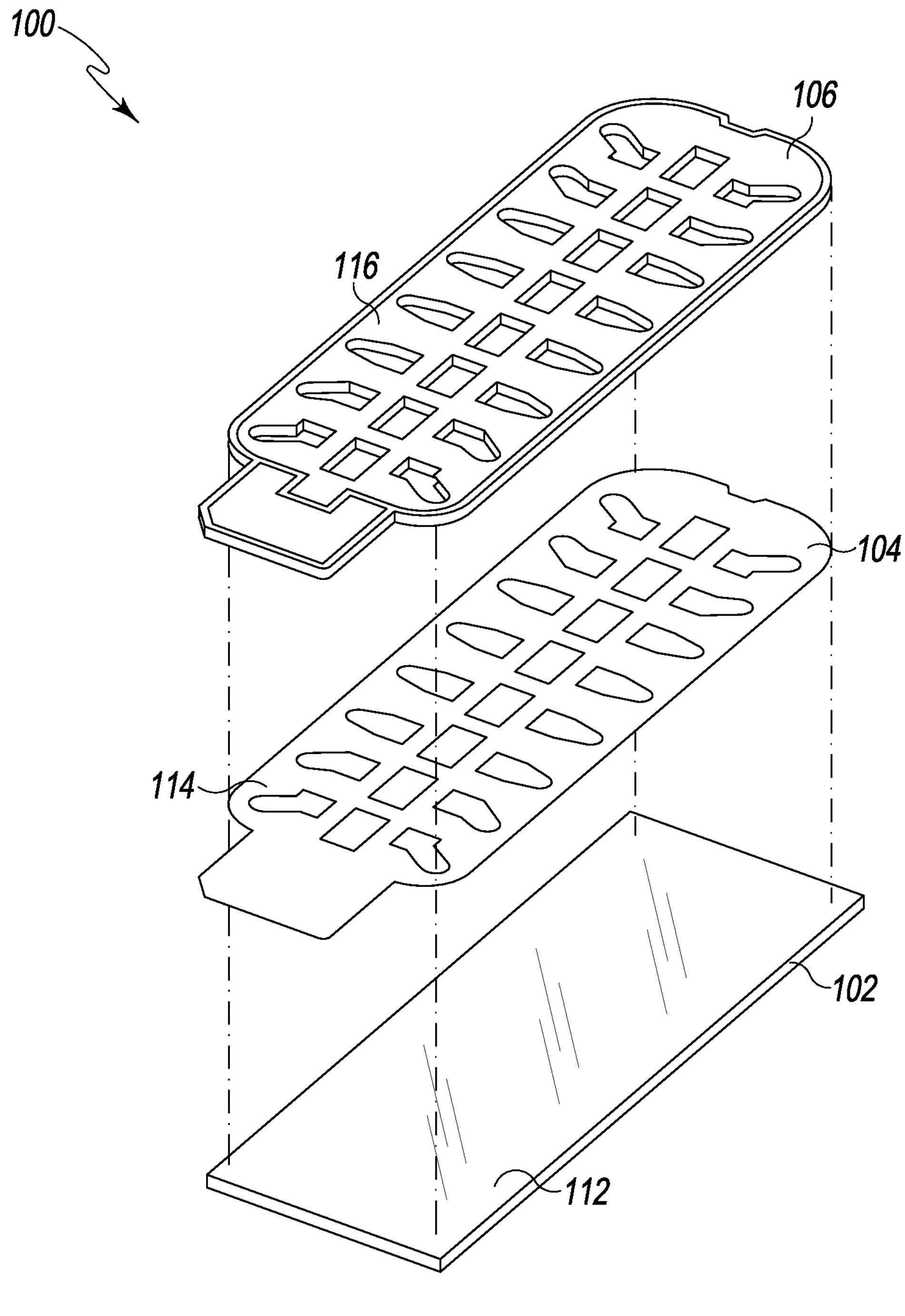
FIG. 1 is an exploded perspective view of one embodiment of a multiplexed microarray.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Multiple embodiments of multiplexed microarrays are disclosed herein. The multiplexed microarrays are usable with standard pipette machines to deposit analyte on the multiplexed microarray in an automated fashion. To maximize or otherwise increase the number of usable microarrays in each multiplexed microarray, the microarrays are located closer to each other than the standard pipette distance of nine millimeters of typical automated pipette machines. To facilitate the use of each microarray, one or more channel layers are used to provide fluid communication between fill ports of the multiplexed microarrays, which are positioned according to the standard pipette applicator distance, and corresponding microarrays as discussed in more detail below. In this way, a larger number of microarrays may be used with standard automated pipette machines and techniques.

Referring now to FIG. 1, in one embodiment, a multiplexed microarray 100 includes a substrate 102, a chamber or chamber layer 104 coupled to the substrate 102, and a compressible port layer 106 coupled to the chamber layer 104. In some embodiments, the chamber layer 104 may be attached or otherwise secured to an upper surface 112 of the substrate 102 via a suitable adhesive. Similarly, the compressible port layer 106 may be attached or otherwise secured to an upper surface 114 of the substrate 102. Additionally, as discussed in more detail below in regard to FIGS. 6 and 7, the port layer 106 may not be compressible in some embodiments.

Figure 2:
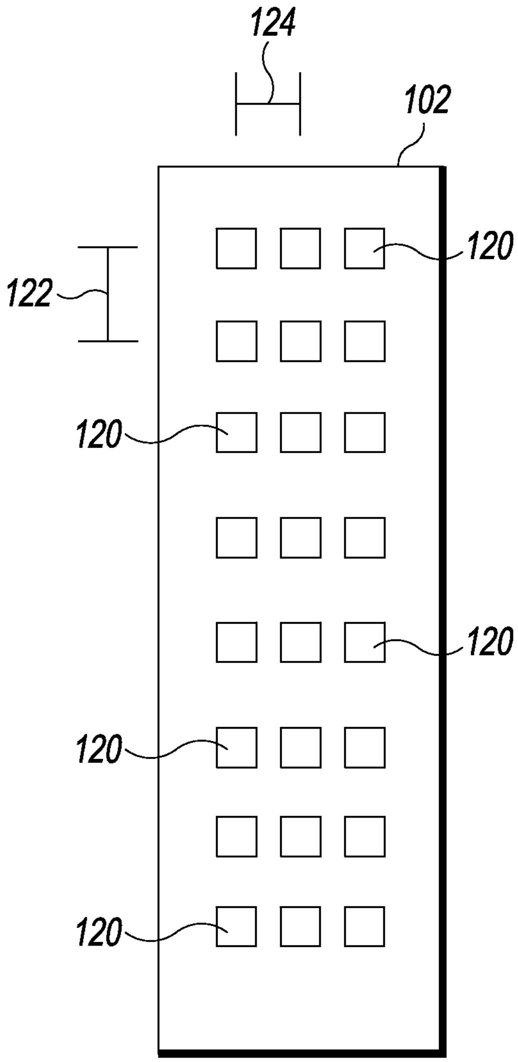
FIG. 2 is a plan view of one embodiment of a substrate of the multiplexed microarray of FIG. 1.
Figure 3:
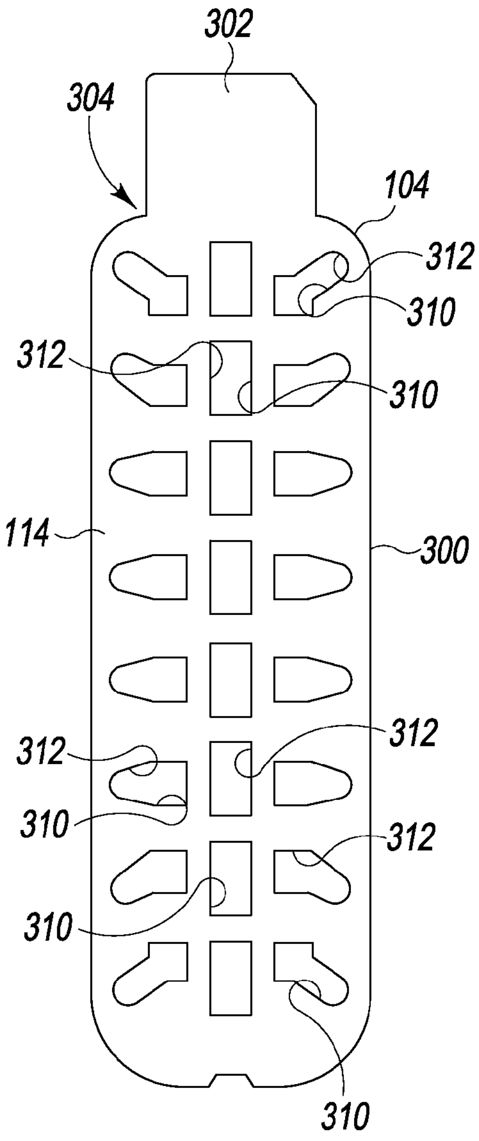
FIG. 3 is a plan view of one embodiment of a physical barrier layer of the multiplexed microarray of FIG. 1.

The substrate 102 may be formed from any solid material suitable for supporting a microarray thereon. For example, the substrate 102 may be embodied as a glass substrate or a silicon substrate in some embodiments. As illustrated in FIG. 2, the substrate 102 includes a plurality of microarrays 120 formed on the upper surface 112. In one embodiment, the microarrays 120 are synthesized on the substrate 102 but other microarray formation techniques may be used in other embodiments. The microarrays 120 may be embodied as any type of microarray used for various testing. For example, in one particular embodiment, the microarrays are embodied as deoxyribonucleic acid (DNA) microarrays, which may be used in, for example, gene expression and discovery, mutation detection, allelic and evolutionary sequence comparison, genome mapping, and other research experiments and analysis. In such embodiments, the microarrays are formed from the DNA oligonucleotides attached to the substrate 102. The DNA oligonucleotide "spots" form probes on the substrate 102, which are used in a hybridization process to investigate samples of interest. Additionally, in other embodiments, the microarrays 120 may be formed using peptides.

In the illustrative embodiment of FIG. 2, the substrate 102 includes twenty-four microarrays 120 spaced apart from each other a longitudinal distance 122 and a lateral distance 124, both of which are less than nine millimeters as measured from the center-to-center of the microarrays 120. For example, in one particular embodiment, the longitudinal distance 122 separating adjacent microarrays is about 7.8 millimeters and the lateral distance 124 is about 5.5 millimeters. However, in other embodiments, the microarrays 120 may be spaced differently. Additionally, in other embodiments, the substrate 102 may include more or less than twenty-four microarrays 120. For example, in some embodiments, the substrate 102 may include eight, sixteen, thirty-two, forty-eight, or a larger number of microarrays 120.

The chamber layer 104 is attached or otherwise coupled to the upper surface 112 of the substrate 102. The chamber layer 104 may be formed from any suitable hydrophobic material including a plastic material such as polyethylene terephthalate (PET), an elastomer such as silicone, polyurethane, or latex, or other hydrophobic material. The chamber layer 104 includes an elongated body 300 and a tab 302 extending from an end 304 of the elongated body 300. The elongated body 300 is sized to cover the upper surface 112 of the substrate 102 when coupled thereto.

The chamber layer 104 also includes a plurality of elongated apertures 310 defined therethough. The apertures 310 are respectively defined by corresponding inner sidewalls 312 of the chamber layer 104. The elongated apertures 310 are located on the chamber layer 104 in a position such that, when the chamber layer 104 is coupled to the substrate 102, each one of the microarrays 120 formed on the substrate 102 is positioned in a corresponding aperture 310. That is, each microarray 120 is laterally surrounded by one of the sidewalls 312 of the chamber layer 104 that defines the corresponding aperture 310.

Figure 4:
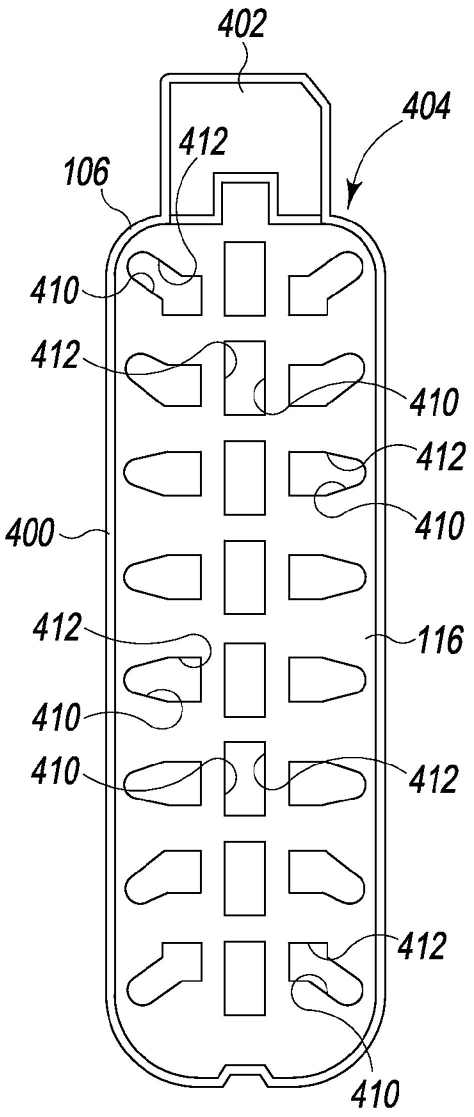
FIG. 4 is a plan view of one embodiment of a compressible layer of the multiplexed microarray of FIG. 1.

Referring now to FIG. 4, the port layer 106 is attached or otherwise coupled to the upper surface 114 of the chamber layer 104. The port layer 106 may be formed from any suitable material capable of forming a pneumatic seal with a cover such as coverplate or sealing film, which may be placed on a top surface 116 of the port layer 106 to seal multiplexed microarray 100. In some embodiments, the coverplate is substantially similar to the substrate 102 and may be formed from any suitable material capable of forming a pneumatic seal with the port layer 106 such as, for example, a glass material.

In one particular embodiment, the port layer 106 is embodied as a compressible, port layer. In such embodiments, the compressible port layer 106 may be formed from any material compressible by the coverplate to form the pneumatic seal as discussed above. For example, the port layer 106 may be formed from a polymer material, such as latex or polyurethane, in some embodiments. However, in other embodiments as discussed below, the port layer 106 may be formed from a non-compressible material.

Similar to the chamber layer 104, the port layer 106 includes an elongated body 400 and a tab 402 extending from an end 404 of the elongated body 400. The elongated body 400 is sized to cover the upper surface 114 of the chamber layer 104 when couple thereto. Additionally, the port layer 106 includes a plurality of elongated apertures 410 defined therethrough. The apertures 410 are respectively defined by corresponding inner sidewalls 412 of the port layer 106. In the illustrative embodiment, the apertures 410 have a substantially identical shape to the apertures 310 of the chamber layer 104. The apertures 410 are located on the port layer 106 such that apertures 410 are congruent with and superimposed over the apertures 310 of the chamber layer 104 when attached or otherwise coupled thereto.

Figure 6:
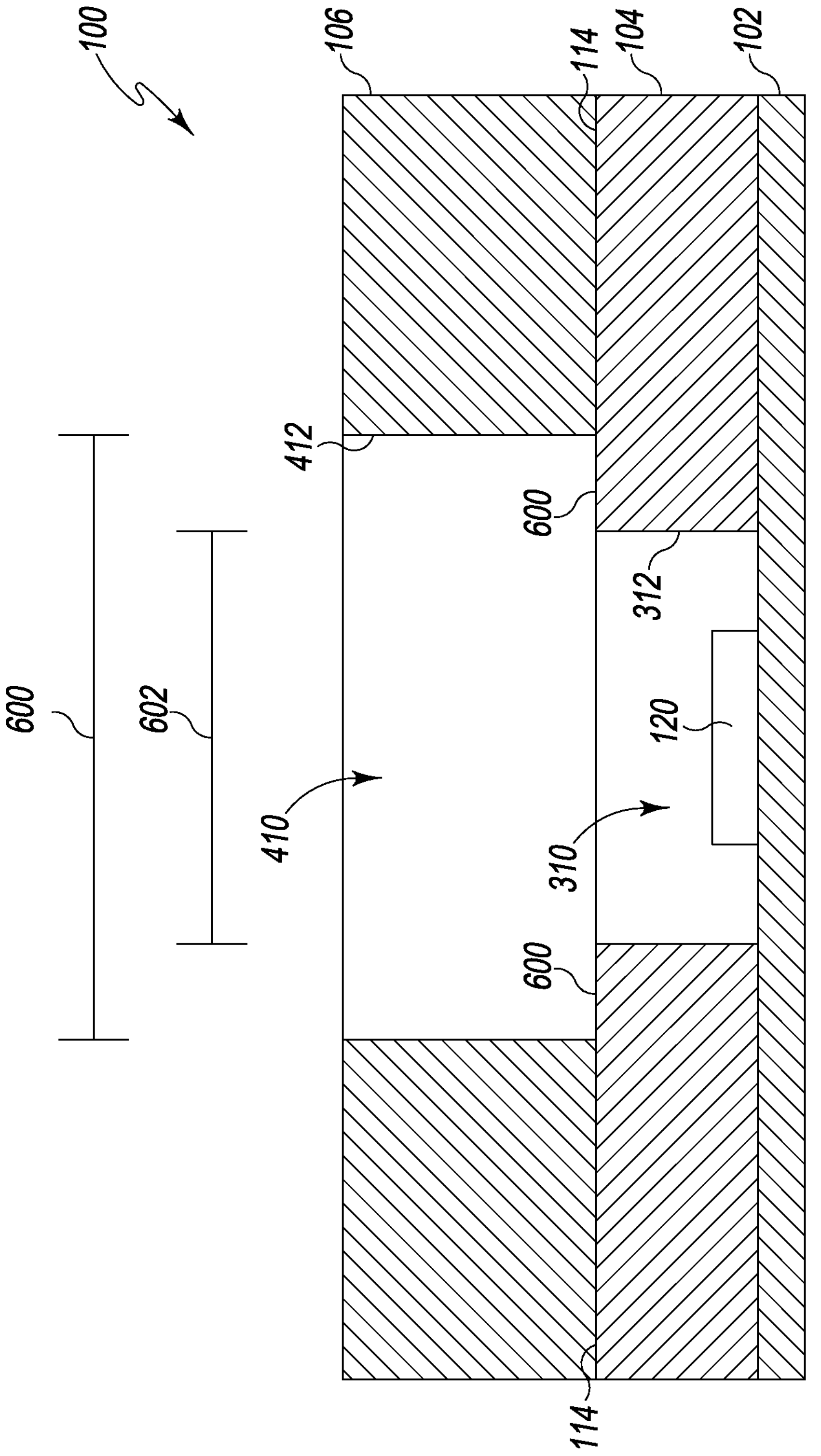
FIG. 6 is a cross-sectional view of another embodiment of the multiplexed microarray of FIG. 1.

In some embodiments as illustrated in FIG. 6, the apertures 410 of the port layer 106 may be laterally larger than the underlying apertures 310 of the chamber layer 104. For example, the apertures 410 have a diameter 600 that is larger than a diameter 602 of the apertures 310 such that the sidewalls 312, 412 are stair-stepped with respect to each other. In such an arrangement, the upper surface 114 of the chamber layer 104 forms a shelve or overhang 604. The shelve or overhang 604 provides an impediment to fluid travelling up the inner sidewalls 412 of the port layer 106 via capillary action or wicking relative to those embodiments in which the apertures 310, 410 are substantially the same size and congruent.

Figure 5:
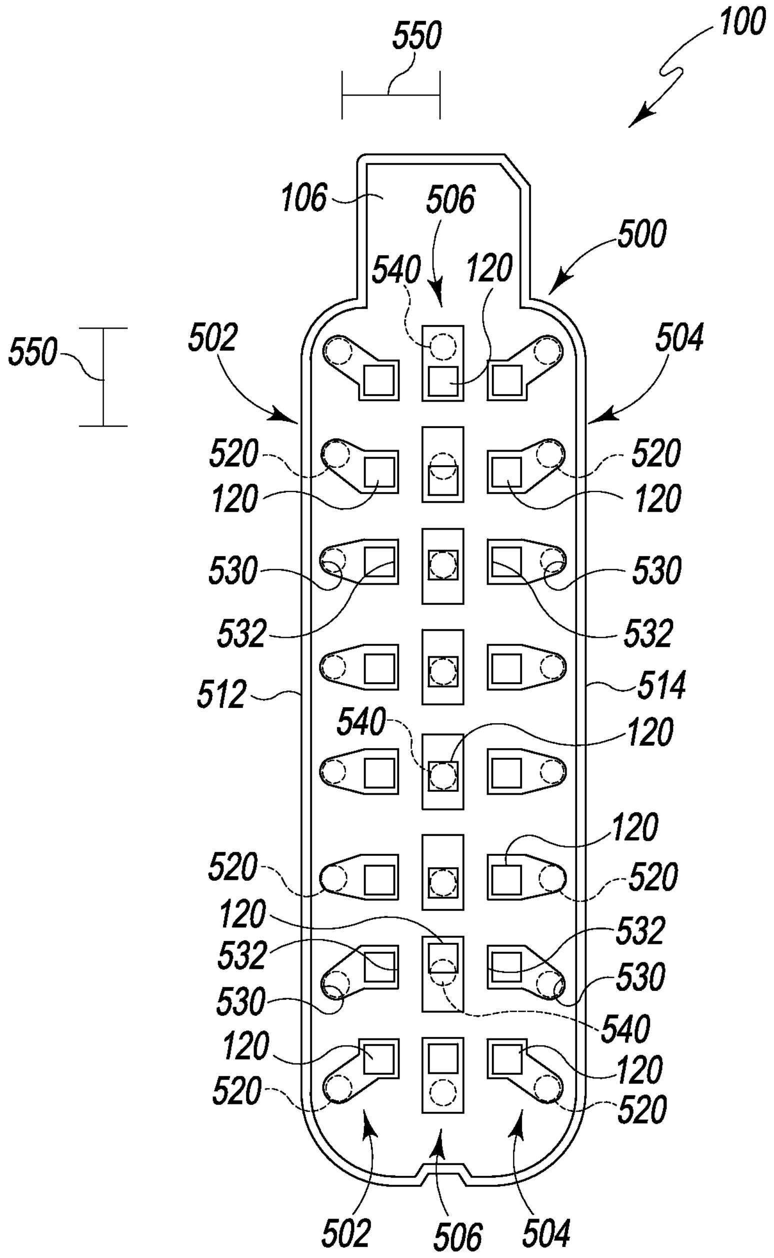
FIG. 5 is a plan view of the multiplexed microarray of FIG. 1 in an assembled configuration.

As illustrated in FIG. 5, when the multiplexed microarray 100 is assembled, the apertures 410 of the port layer 106, the apertures 310 of the chamber layer 104, and the upper surface 112 of the substrate 102 cooperate to define a plurality of corresponding elongated wells 500. That is, the elongated wells 500 are defined by the sidewall 412 of the port layer 106, the sidewalls 312 of the chamber layer 104, and the upper surface 112 of the substrate 102. The elongated wells 500 are shaped such that the planar cross-sectional area or "footprint" of each well 500 is substantially equal. As such, the volume defined by the sidewalls 312, 412 of the elongated wells 500 and the upper surface 112 of the substrate 102 are substantially equal. Accordingly, equal volumes of analyte will fill each well 500 to a substantially equal height regardless of the particular planar shape of the well 500 (i.e., the shape of the perimeter defined by the sidewalls 312, 412).

The elongated wells 500 include a plurality of laterally located wells 502, a plurality of laterally located wells 504, and a plurality of centrally located wells 506. Specifically, the wells 502 are located toward a longitudinal side 512 of the multiplexed microarray 100 and the wells 504 are located toward a longitudinal side 514 of the multiplexed microarray 100. Additionally, the wells 506 are located toward the longitudinal center of the multiplexed microarray 100 and between the wells 502, 504. However, in other embodiments, other configurations of the wells 500 may be used.

Each of the wells 502, 504 includes an outer lateral end 530 and an inner lateral end 532. The outer lateral end 530 of each well 502, 504 is located toward the corresponding longitudinal side 512, 514 of the multiplexed microarray 100. The inner lateral end 532 of the each well 502, 504 is located toward the longitudinal center of the multiplexed microarray 100. As shown in FIG. 5, each of the wells 502, 504 includes one of the microarrays 120 located therein. In particular, a microarray 120 is located at the inner lateral end 532 of each well 502, 504 of the elongated wells 500. The outer lateral end 530 of each well 502, 504 forms a fill port or location 520 to receive an analyte. The fill port 520 (i.e., outer lateral end 530) is spaced apart from but in fluid communication with the inner lateral end 532 at which the associated microarray 120 is located.

Similar to the laterally located wells 502, 504, each of the centrally located wells 506 include a corresponding microarray 120 located therein. As illustrated in FIG. 5, depending on the particular location of the well 506, the corresponding microarray 120 may be located toward a lateral end or the center of the associated well 506. Additionally, each well 506 includes an associated fill port or location 540. Again, depending on the particular location of the well 506, the fill port 540 may be located vertically over the microarray 120 (e.g., those wells 506 located toward the longitudinal center of the multiplexed microarray 100) or may be lateral offset or separated from the microarray 120 (e.g., those wells 506 located toward the longitudinal ends of the multiplexed microarray 100). Similar to the fill ports 520, the fill ports or locations 540 are in fluid communication with the associated microarray 120 regardless of the particular position of the fill port 540 with respect to the associated microarray 120.

It should be appreciated that in the illustrative embodiment the fill ports 520, 540 are located or otherwise defined in the multiplexed microarray 100 according to the pipette distance of standard automated pipette machines. For example, in the illustrative embodiment of FIG. 5, each fill port 520, 540 is spaced apart or otherwise located away from each other a distance 550 (i.e. a center-to-center distance) of about nine millimeters. As such, although the microarrays 120 are spaced apart a distance less than nine millimeters, the multiplexed microarray 100 is usable with standard automated pipette machines having pipette applicator spacing of nine millimeters or similar. Additionally, the analyte deposited at the fill ports 520, 540 using such automated pipette machines contacts the microarrays 120 because the fill ports 520, 540 are in fluid communication with the associated microarray 120.

Figure 7:
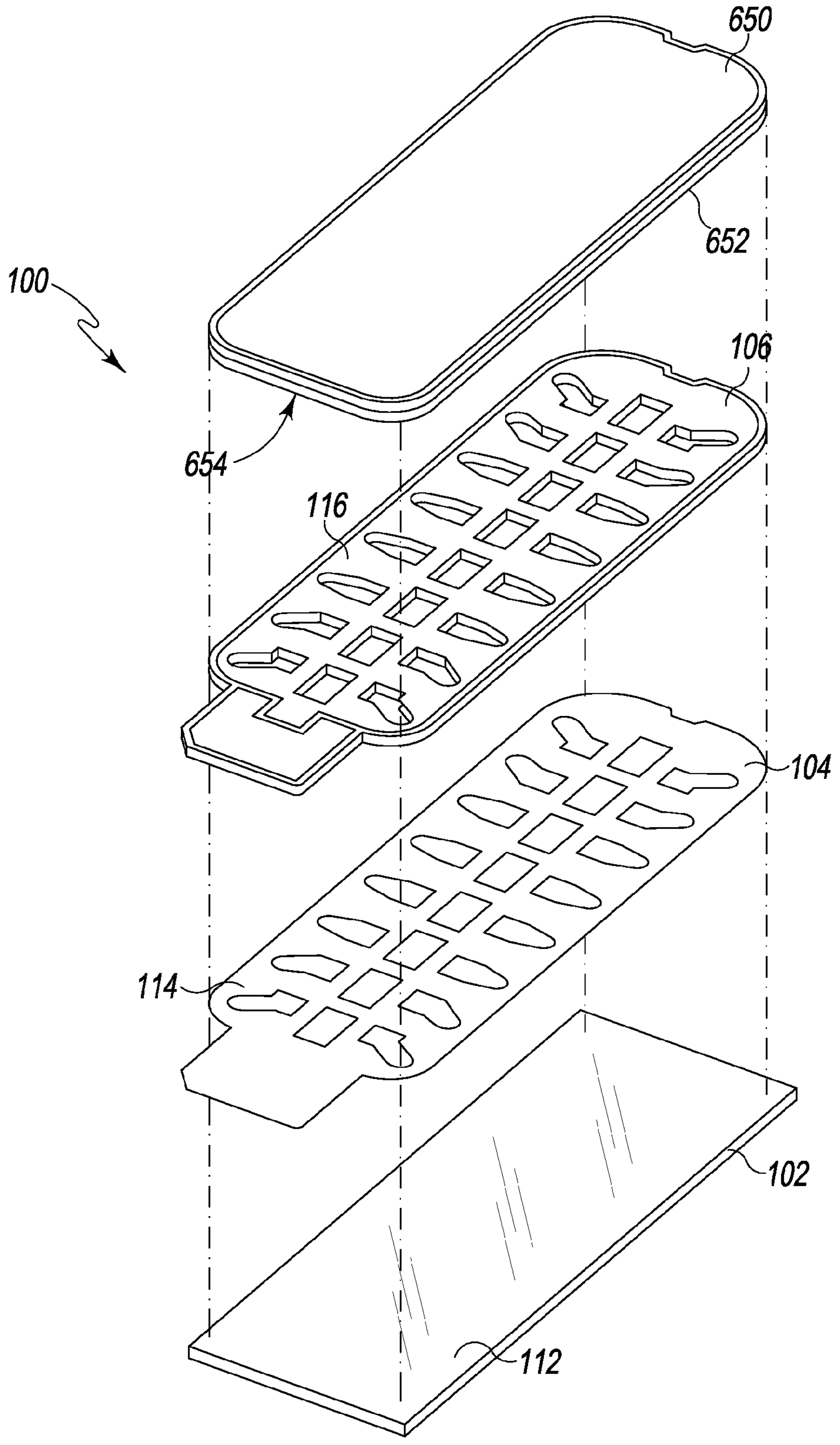
FIG. 7 is an exploded perspective view of another embodiment of the multiplexed microarray of FIG. 1.
Figure 8:
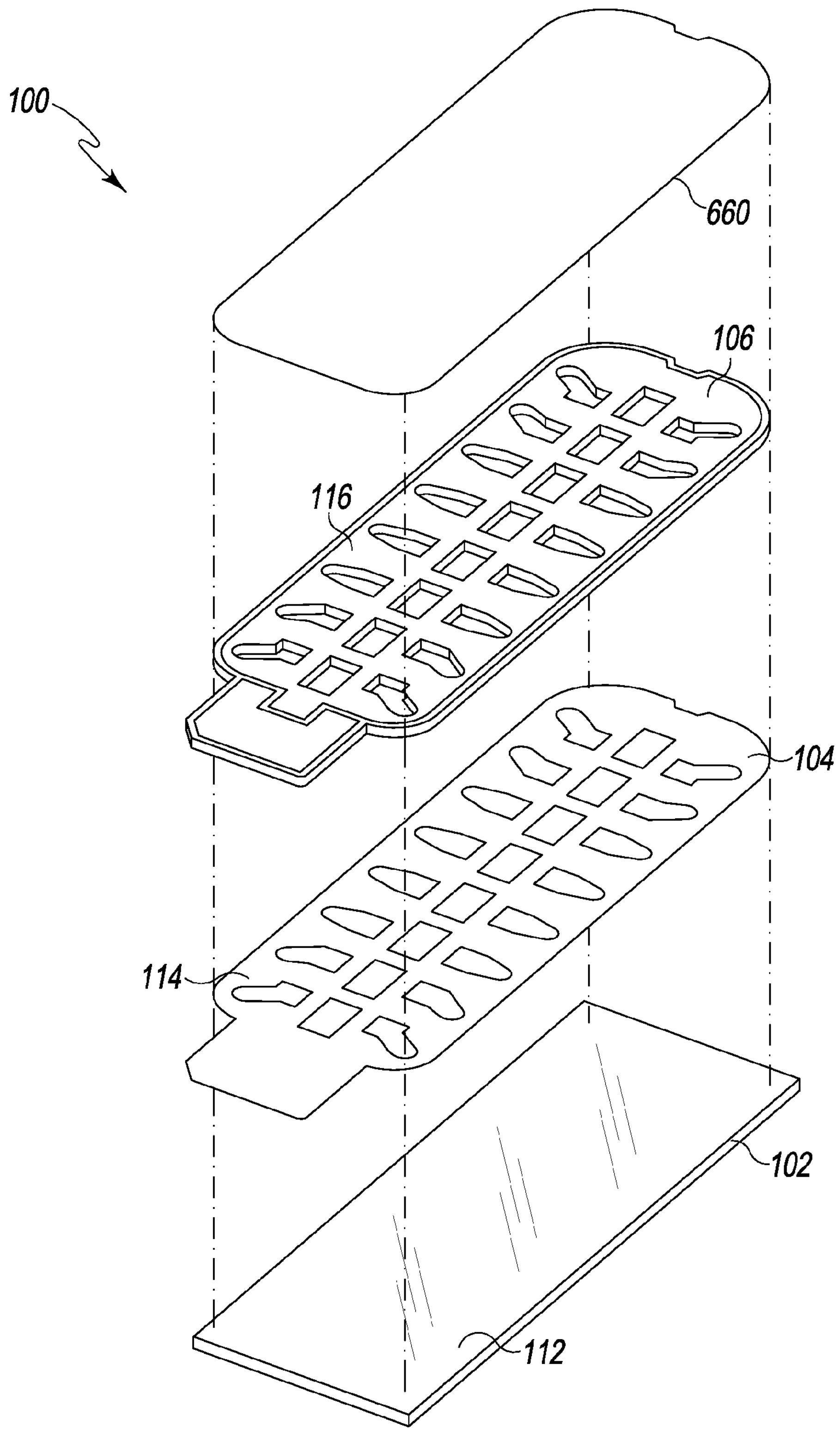
FIG. 8 is an exploded perspective view of another embodiment of the multiplexed microarray of FIG. 1.

Referring now to FIG. 7, as discussed above, the port layer 106 may be non-compressible in some embodiments. In such embodiments, a coverplate 650 may be used to seal the multiplexed microarray 100. In the illustrative embodiment, the coverplate 650 is formed from a rigid material and includes a sealing gasket 652 secured to a bottom surface 654 of the coverplate 650. The sealing gasket 652 forms a compressible layer that seals the wells 500 when the coverplate 650 is secured to the port layer 106. Alternatively, as illustrated in FIG. 8, a sealing film 660 may be used to seal the multiplexed microarray 100. To do so, the sealing film 660 may be placed over the top surface 116 of the port layer 106 and sealed to the layer 106 via adhesives or a heat-seal. Although the sealing film 660 is sized to cover a single multiplexed array 100 in the illustrative embodiment of FIG. 8, the sealing film 660 may be sized to cover multiple multiplexed arrays 100 in other embodiments.

Figure 9:
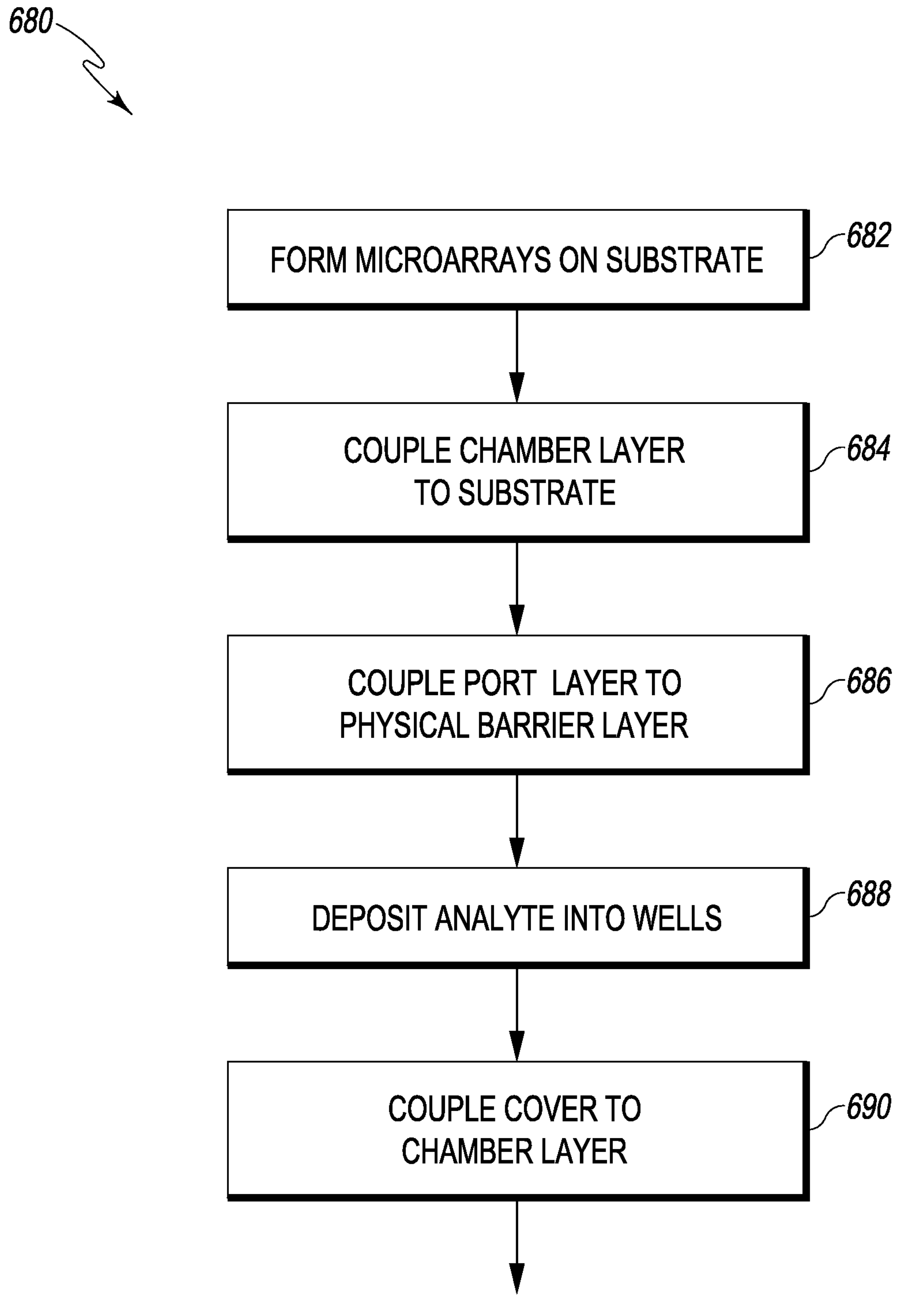
FIG. 9 is a simplified flow diagram of one embodiment of a method for fabricating the multiplexed microarray of FIGS. 1, 7, and/or 8.

Referring now to FIG. 9, a method 680 for fabricating and using the multiplexed microarray 100 of FIGS. 1-5 begins with block 682. In block 682, the microarrays 120 are formed on the upper surface 112 of the substrate 102. In the illustrative embodiment, the microarrays 120 are synthesized on the substrate 102 but other microarray formation techniques may be used in other embodiments. The microarrays 120 are positioned on the substrate 102 such that each microarray 120 is spaced apart from an adjacent microarray a distance less than nine millimeters as discussed above in regard to FIG. 2. In the illustrative embodiment, twenty-four microarrays 120 are formed on the substrate 102 in block 682. However, in other embodiments, a greater or fewer number of microarrays 120 may be formed on the substrate 102.

In block 684, the chamber layer 104 is coupled to the upper surface 112 of the substrate 102. For example, in the illustrative embodiment, the chamber layer 104 is attached or otherwise secured to the substrate 102 via a suitable adhesive. The chamber layer 104 is positioned on the substrate 102 such that each microarray 120 located on the substrate 102 is received in a corresponding aperture 310 of the chamber layer. 104. That is, the sidewalls 312 that define the apertures 310 of the chamber layer 104 surround the corresponding microarray 120 thereby forming an initial well.

In block 686, the port layer 106 is coupled to the upper surface 114 of the chamber layer 104. For example, in the illustrative embodiment, the port layer 106 is attached or otherwise secured to the chamber layer 104 via a suitable adhesive. The port layer 106 is positioned on the chamber layer 104 such that each aperture 410 of the port layer 106 is superimposed over and congruent with a corresponding aperture 310 of the chamber layer 104. As discussed above, the apertures 310, 410 (i.e., the sidewalls 312, 412 that define the apertures 310, 410) and the upper surface 112 of the substrate 102 cooperate to define the elongated wells 500.

After the multiplexed microarray 100 has been assembled as discussed above, an analyte may be deposited in each elongated well 500 in block 688. To do so, the multiplexed microarray 100 may be used with a standard automated pipette machine having, for example, a pipette spacing of nine millimeters. The analyte is deposited in the fill port or locations 520, 540, which may be laterally offset from the microarray 120 of the associated elongated well 500 as discussed above. However, because the fill ports 520, 540 are in fluid communication with each associated microarray 120, the analyte also contacts the microarray 120. Additionally, because each elongated well 500 has a substantially equal lateral cross-sectional area, identical volumes of analyte will fill each well 500 to substantially the same height.

After the analyte has been deposited in block 688, a cover may be placed on or otherwise coupled to the top surface 116 of the port layer 106. In embodiments similar to the embodiment of FIG. 1 in which the port layer 106 is formed from a compressible material, the cover may be embodied as a coverplate. In such embodiments, the coverplate may be substantially similar to the substrate 102 (e.g., a glass slide). The coverplate and the compressible, port layer 106 form a pneumatic seal to seal each of the elongated wells 500. To do so, a downwardly pressure may be applied to the coverplate to compress the port layer 106 to form the pneumatic seal. Alternatively, in embodiments similar to the embodiment of FIG. 7 in which the port layer 106 is not compressible, the coverplate 650 may be coupled to the top surface 116. The sealing gasket 652 of the coverplate 650 forms a pneumatic seal with the port layer 106 to seal each of the elongated wells 500. Again, a downward pressure may be applied to the coverplate 650 to compress the seal gasket 652 against the port layer 106 to form the pneumatic seal. However, in embodiments similar to the embodiment of FIG. 8, the cover may be embodied as a sealing film 660. As discussed above, the sealing film 660 may be attached to the top surface 116 of the port layer 106 via adhesives or a heat-seal to seal the elongated wells 500. Regardless of the particular embodiment, after the cover has been coupled to the port layer 106, the multiplexed microarray 100 may be hybridized to perform the desired sample analysis.

Figure 10:
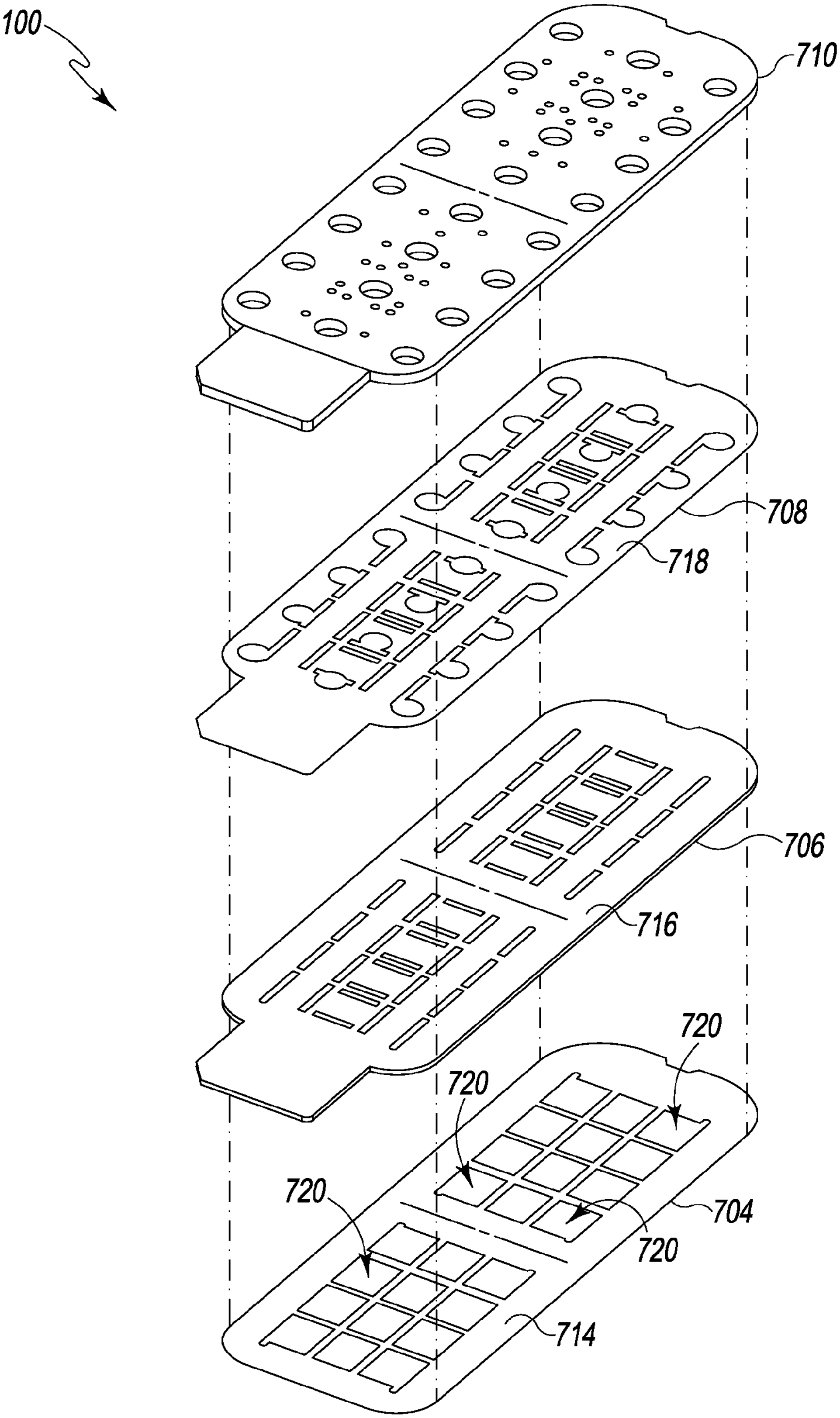
FIG. 10 is an exploded perspective view of another embodiment of a multiplexed microarray.

In the embodiment of FIGS. 1-8, the multiplexed microarray 100 includes a single chamber layer. However, in other embodiments, the multiplexed microarray 100 may include multiple layers of various chamber/channel geometry. For example, in another embodiment illustrated in FIGS. 10-14, the multiplexed microarray 100 includes the substrate 102 (not shown in FIG. 10), a chamber layer 704, a lower channel layer 706, an upper channel layer 708, and a port layer 710. The chamber layer 704 is coupled or otherwise attached to the upper surface 112 of the substrate 102. Similarly, the lower channel layer 706 is coupled to or otherwise attached to an upper surface 714 of the chamber layer 704. The upper channel layer 708 is coupled or otherwise attached to an upper surface 716 of the lower channel layer 706, and the port layer 710 is coupled or otherwise attached to an upper surface 718 of the upper channel layer 708.

Figure 11:
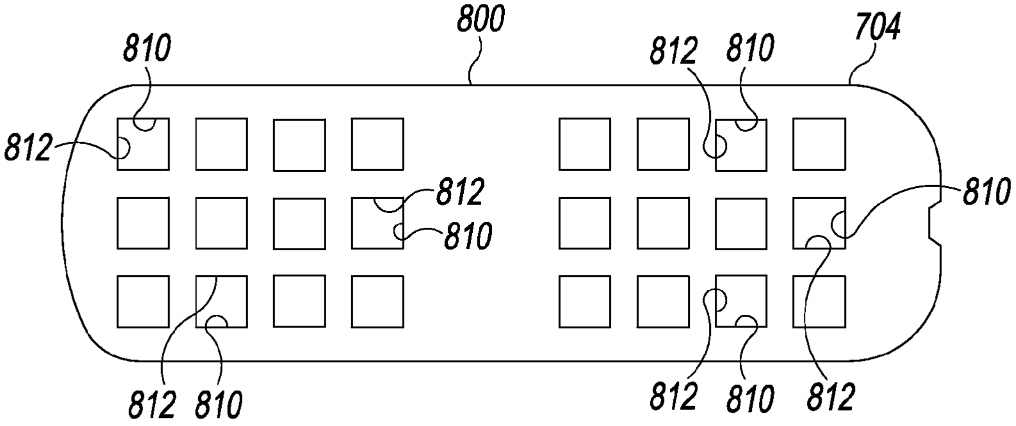
FIG. 11 is a plan view of one embodiment of a chamber layer of the multiplexed microarray of FIG. 10.

Similar to the chamber layer 104, the chamber layer 704 may be formed from any suitable hydrophobic material including a plastic material such as polyethylene terephthalate (PET), an elastomer such as silicone, polyurethane, or latex, or other hydrophobic material. The chamber layer 704 includes an elongated body 800 as illustrated in FIG. 11. The elongated body 800 is sized to cover the upper surface 112 of the substrate 102 when coupled thereto. The chamber layer 704 also includes a plurality of apertures 810 defined therethough. The apertures 810 are respectively defined by corresponding inner sidewalls 712 of the chamber layer 704. Illustratively, the apertures 810 have a square or rectangular shape but may have other shapes in other embodiments. The apertures 810 are located on the chamber layer 704 in a position such that, when the chamber layer 704 is coupled to the substrate 102, each one of the microarrays 120 formed on the substrate 102 is positioned in a corresponding aperture 810. That is, each microarray 120 is laterally surrounded by one of the sidewalls 812 of the chamber layer 704 that defines the corresponding aperture 810 to form a microarray chamber 720. Each microarray chamber 720 has a substantially equal lateral cross-sectional area such that identical volumes of analyte fill each microarray chamber 720 to substantially the same height.

Figure 12:
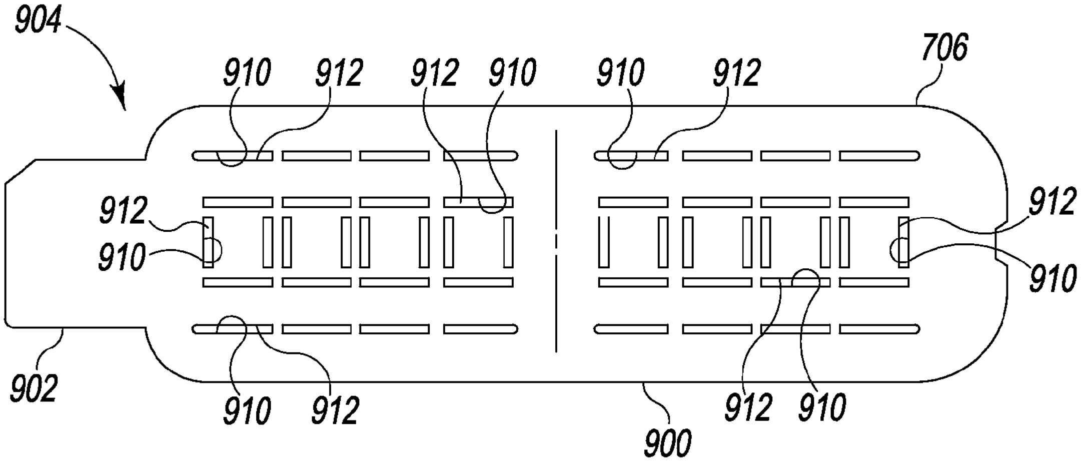
FIG. 12 is a plan view of one embodiment of a channel layer of the multiplexed microarray of FIG. 10.

Referring now to FIG. 12, the lower channel layer 706 provides a fluid channel between the upper channel layer 708 and the chamber layer 704. In the illustrative embodiment, the lower channel layer 706 is relatively thin and formed from a plastic material. The lower channel layer 706 includes an elongated body 900 and a tab 902 extending from an end 904 of the elongated body 900. The elongated body 900 is sized to cover the upper surface 714 of the chamber layer 704 when couple thereto.

The lower channel layer 706 includes a plurality of elongated apertures or slits 910 define therethrough. The apertures 910 are respectively defined by corresponding inner sidewalls 912 of the channel layer 706. The apertures or slits 910 form vertical channels through the lower channel layer 706 and are shaped and sized to allow flow of analyte when applied to the multiplexed microarray 100. In the illustrative embodiment, the apertures 910 are shaped differently from the apertures 810 of the chamber layer 104. That is, the apertures 910 are embodied as elongated slits and the apertures 810 are square or rectangular in shape. The apertures or slits 910 are located in the lower channel layer 706 such that apertures 910 are superimposed over the apertures 810 of the chamber layer 704 when attached or otherwise coupled thereto. In the illustrative embodiment, the lower channel layer 706 includes a greater number of apertures 910 than the number of apertures 810 defined through the chamber layer 704. As such, two apertures or slits 910 are superimposed over each aperture 810 of the chamber layer 704 when the lower channel layer 706 is coupled thereto. As discussed in more detail below, one of each pair of slits 910 positioned over each aperture 810 forms a vent channel to allow air to flow out of each associated microarray chamber 720.

Figure 13:
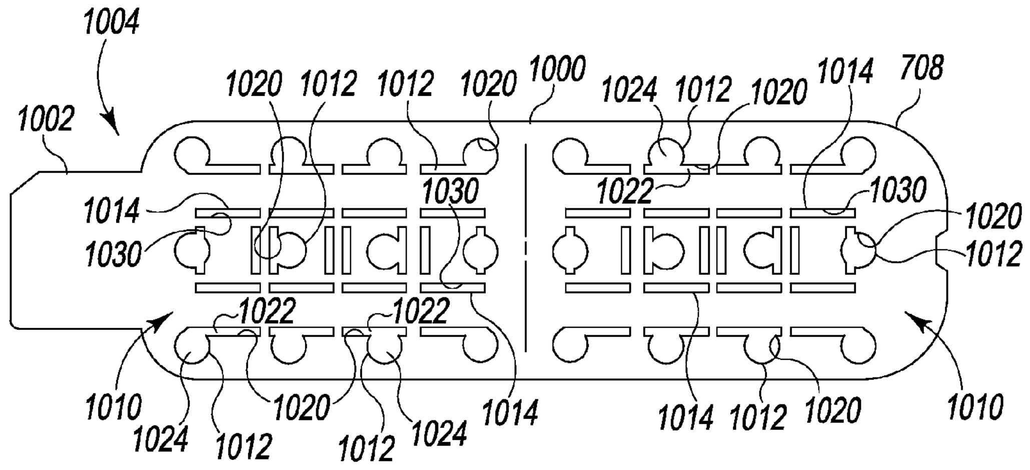
FIG. 13 is a plan view of one embodiment of another channel layer of the multiplexed microarray of FIG. 10.

Referring now to FIG. 13, the upper channel layer 708 provides a fluid channel between the port layer 710 and the lower channel layer 706. The upper channel layer 708 may be formed from any suitable plastic material that may be adhered to the port layer 710. In one particular embodiment, the upper channel layer 708 is formed from a polymer material.

The upper channel layer 708 includes an elongated body 1000 and a tab 1002 extending from an end 1004 of the elongated body 1000. The elongated body 1000 is sized to cover the upper surface 716 of the lower channel layer 706 when couple thereto. The upper channel layer 708 also includes a plurality of apertures 1010 defined therethrough. The apertures 1010 include a plurality of fluid channel apertures 1012 and a plurality of vent apertures 1014. The fluid channel apertures 1012 form vertical channels through the upper channel layer 708 and are shaped and sized to allow flow of an analyte when applied to the multiplexed microarray 100. The fluid channel apertures 1012 are respectively defined by corresponding inner sidewalls 1020. Each fluid channel aperture 1012 includes an elongated slit 1022 and an opening 1024 in fluid communication with the elongated slit 1022. Illustratively, the opening 1024 is embodied as a circular opening having a width greater than the width of the associated elongated slit 1022 but may have other shapes in other embodiments. Similarly, the vent apertures 1014 form vertical channels through the upper channel layer 708 and are shaped and sized to allow airflow from the microarray chamber 720 when an analyte is applied to the multiplexed microarray 100. The vent apertures 1014 are respectively defined by corresponding inner sidewalls 1030 and embodied as elongated slits or openings.

When the upper channel layer 708 is coupled to the lower channel layer 706, the apertures 1010 are superimposed over the apertures 910 of the lower channel layer 706. In particular, each of the fluid channel apertures 1012 and associated vent aperture 1014 are superimposed over one of the pair of slits or apertures 910 of the lower channel layer 706, which are located above each microarray chamber 720. As such, the fluid channel aperture 1012 and corresponding aperture 910 form a fluid channel to the associated microarray chamber 720 and the vent aperture 1014 and corresponding aperture 910 form a vent channel to allow air to flow out of the associated microarray chamber 720 during filling of the chamber 720 with analyte.

Figure 14:
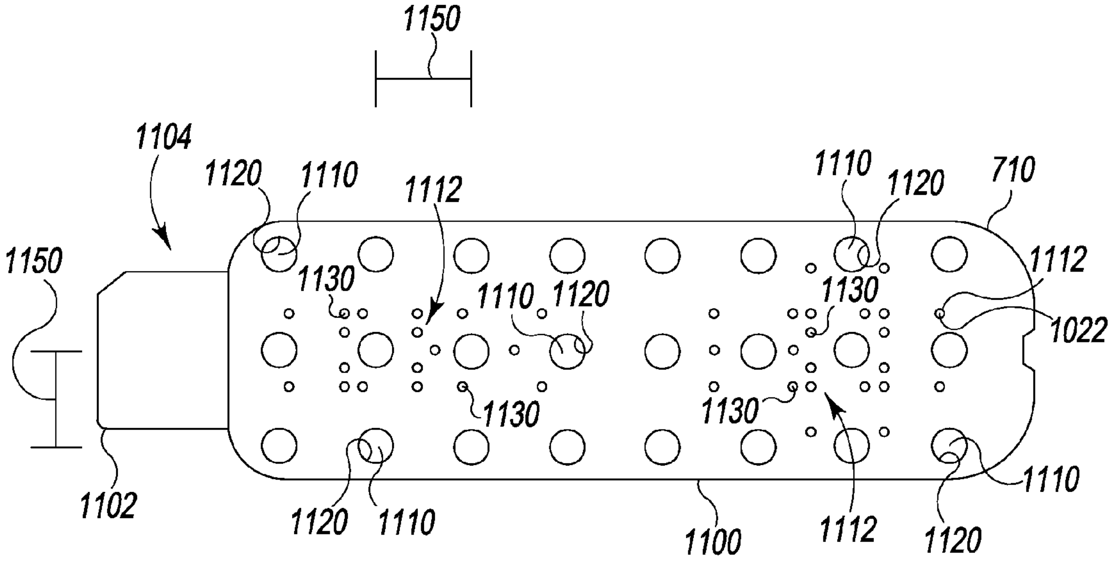
FIG. 14 is a plan view of one embodiment of a port layer of the multiplexed microarray of FIG. 10.

Referring now to FIG. 14, the port layer 710 is coupled to the upper surface 718 of the upper channel layer 708. The port layer 710 may be formed from any suitable material capable of forming a seal with the upper channel layer 708. In the illustrative embodiment, the port layer 710 is formed from a compressible material but may be formed from other materials in other embodiments. The port layer 710 includes an elongated body 1100 and a tab 1102 extending from an end 1104 of the elongated body 1100. The elongated body 1100 is sized to cover the upper surface 718 of the upper channel layer 708 when couple thereto.

The port layer 710 includes a plurality of fill ports 1110 defined therethrough. The fill ports 1110 form vertical channels through the port layer 710 and are sized and shaped to allow flow of an analyte to the microarray chamber 720 as discussed below. The fill ports 1110 are respectively defined by corresponding inner sidewalls 1120. Illustratively, the fill ports 1110 are embodied as circular openings but may have other shapes in other embodiments. The fill ports 1110 are located on the port layer 710 such that, when the port layer 710 is coupled to the upper channel layer 708, each fill port 1110 is superimposed over a corresponding fluid channel aperture 1012 of the upper channel layer 708. Additionally, it should be appreciated that, in the illustrative embodiment, the fill ports 1110 are located or otherwise defined in the port layer 710 according to the pipette distance of standard automated pipette machines. For example, in the illustrative embodiment of FIG. 11, each fill port 1110 is spaced apart or otherwise located away from each other a distance 1150 (i.e., a center-to-center distance) of about nine millimeters. As such, although the microarrays 120 are spaced apart a distance less than nine millimeters on the substrate 102, the multiplexed microarray 100 is usable with standard automated pipette machines having pipette spacing of nine millimeters or similar.

The port layer 710 also includes a plurality of vent ports 1112 defined therethrough. The vent ports 1112 form vertical channels through the port layer 710 and are sized and shaped to allow flow of air from the microarray chamber 720 during filling of the chamber 720 with an analyte. The vent ports 1112 are respectively defined by corresponding inner sidewalls 1130. Illustratively, the vent ports 1112 are embodied as circular openings but may have other shapes in other embodiments. The vent ports 1112 are located on the port layer 710 such that, when the port layer 710 is coupled to the upper channel layer 708, each vent port 1112 is superimposed over a corresponding fluid channel aperture 1012 or vent channel aperture 1014 of the upper channel layer 708 depending on the positioning of the vent port 1112. The port layer 710 may include any number of vent ports 1112 to facilitate the loading of analyte into the multiplexed microarray 100.

As described above, the multiplexed microarray 100 of FIGS. 10-14 includes multiple channel layers 706, 708 located between the chamber layer 704 and the port layer 710. However, in other embodiments additional or fewer channel layers may be used. For example, in some embodiments, the channel layer 706 may be omitted from the multiplexed microarray 100. In such embodiments, the channel layer 708 is coupled directly to the upper surface 714 of the chamber layer 704. Additionally, in other embodiments, channel layers having other channel geometry may be used to facilitate the loading of analyte into the microarray chamber 720 and movement of air out of the wells. For example, channels may be used to connect vent ports from the wells to a common exit port that is separated from sidewalls that would encourage wicking to the coverplate/sealing film.

Figure 15:
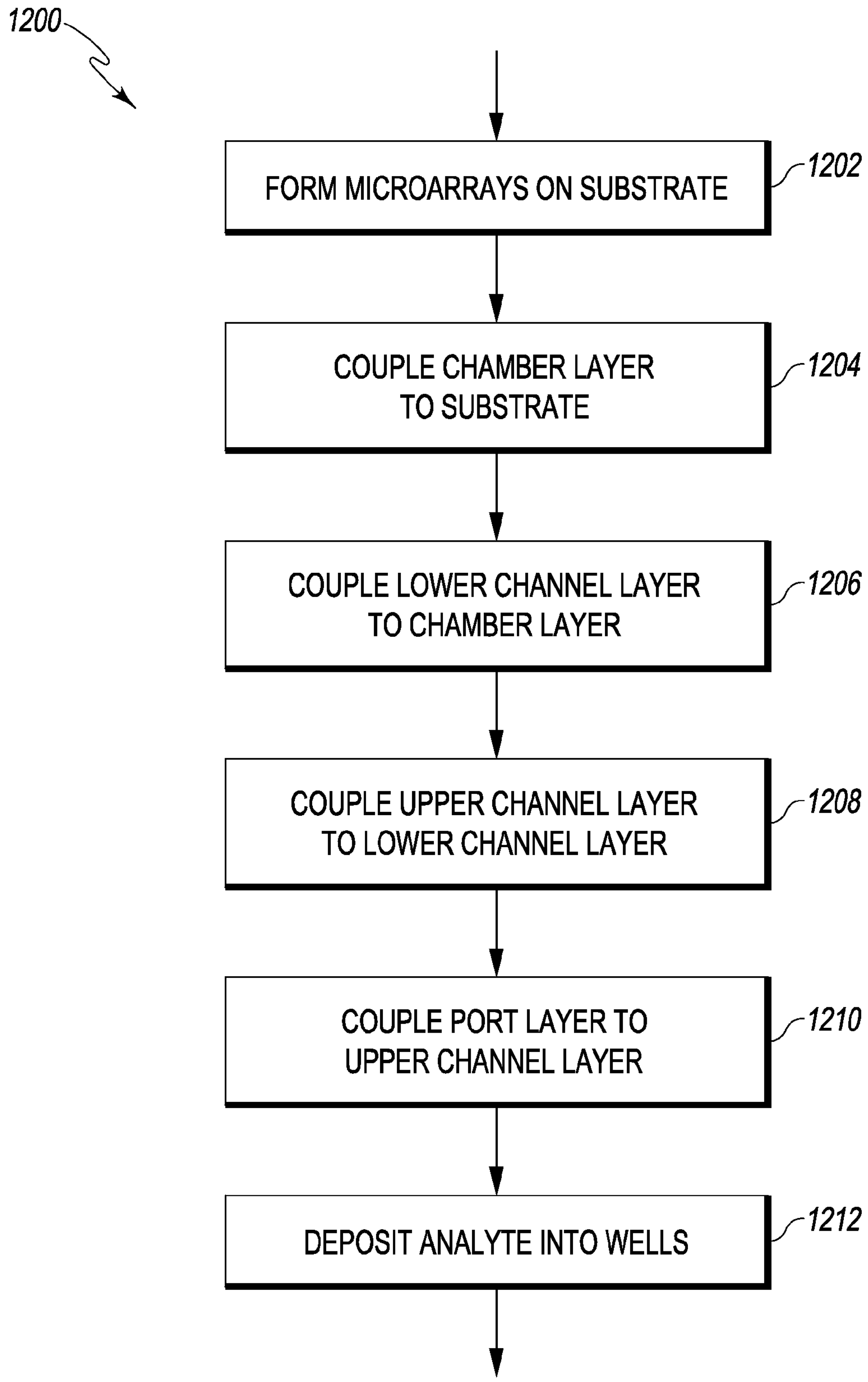
FIG. 15 is a simplified flow diagram of one embodiment of a method for fabricating the multiplexed microarray of FIG. 10.
Figure 16:
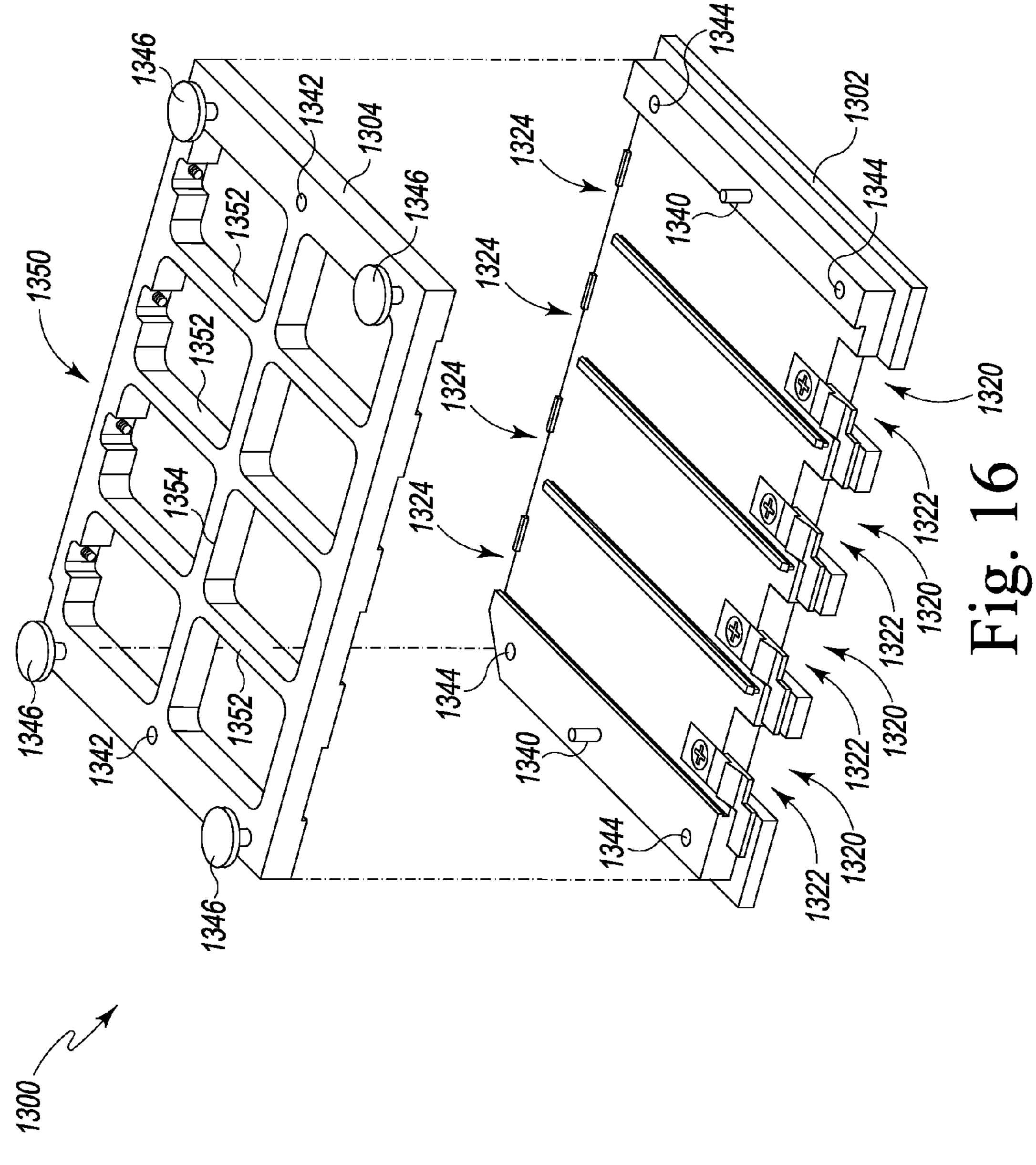
FIG. 16 is an exploded perspective view of one embodiment of a multiplexed microarray cassette.

Referring now to FIG. 15, a method 1200 for fabricating and using the multiplexed microarray 100 of FIGS. 7-11 begins with block 1202. In block 1202, the microarrays 120 are formed on the upper surface 112 of the substrate 102. In the illustrative embodiment, the microarrays 120 are synthesized on the substrate 102 but other microarray formation techniques may be used in other embodiments. As discussed above in regard to block 602 of method 600, the microarrays 120 are positioned on the substrate 102 such that each microarray 120 is spaced apart from an adjacent microarray a distance less than nine millimeters. In the illustrative embodiment, twenty-four microarrays 120 are formed on the substrate 102 in block 1202. However, in other embodiments, a greater or fewer number of microarrays 120 may be formed on the substrate 102.

In block 1204, the chamber layer 704 is coupled to the upper surface 112 of the substrate 102. For example, in the illustrative embodiment, the chamber layer 704 is attached or otherwise secured to the substrate 102 via a suitable adhesive. The chamber layer 704 is positioned on the substrate 102 such that each microarray 120 located on the substrate 102 is received in a corresponding aperture 810 of the chamber layer 704. That is, the sidewalls 812 that define apertures 810 of the chamber layer 704 surround the corresponding microarray 120 thereby forming the associated microarray chamber 720.

In block 1206, the lower channel layer 706 is coupled to the upper surface 714 of the chamber layer 704. For example, in the illustrative embodiment, the lower channel layer 706 is attached or otherwise secured to the chamber layer 704 via a suitable adhesive. The lower channel layer 706 is positioned on the chamber layer 704 such that each elongated aperture or slit 910 of the lower channel layer 706 is superimposed over a corresponding aperture 810 of the chamber layer 704.

In block 1208, the upper channel layer 708 is coupled to the upper surface 716 of the lower channel layer 706. For example, in the illustrative embodiment, the upper channel layer 708 is attached or otherwise secured to the lower channel layer 706 via a suitable adhesive. The upper channel layer 708 is positioned on the lower channel layer 706 such that each aperture 1010 of the upper channel layer 708 is superimposed over a corresponding elongated aperture or slit 910 of the lower channel layer 706.

In block 1210, the port layer 710 is coupled to the upper surface 718 of the upper channel layer 708. The port player 710 is attached or otherwise secured to the upper layer 708 via a suitable adhesive. The port layer 710 is positioned on the upper channel layer 708 such that each aperture 1110 of the port layer 710 is superimposed over a corresponding aperture 1024 of the upper channel layer 708.

After the multiplexed microarray 100 has been assembled as discussed above, an analyte may be deposited in each microarray chamber 720 in block 1212. To do so, the multiplexed microarray 100 may be used with a standard automated pipette machine having, for example, a pipette spacing of nine millimeters. The analyte is deposited in the fill ports 1110, which may be laterally offset from the microarray 120 located in the associated microarray chamber 720 as discussed above. However, because the fill ports 1110 are in fluid communication with each microarray chamber 720 and associated microarray 120, the deposited analyte also contacts the associated microarray 120. Additionally, because each microarray chamber 720 has a substantially equal lateral cross-sectional area, identical volumes of analyte will fill each microarray chamber 720 to substantially the same height. After the analyte has been deposited in block 1212, a cover may be placed over the microarray 100. As discussed above, the cover may be embodied as a non-compressible coverplate, a compressible coverplate (e.g., coverplate 650), or a sealing film (e.g., sealing film 660). Subsequently, the multiplexed microarray 100 may be hybridized to perform the desired sample analysis.

Referring now to FIGS. 16-19, multiple multiplexed microarrays 100 may be used with a multiplexed microarray cassette 1300 to perform a large number of assays at a given time. For example, in the illustrative multiplexed microarray cassette 1300 is configured to receive up to four multiplexed microarrays 100. However, in other embodiments, the multiplexed microarray cassette 1300 may be configured to hold more or fewer multiplexed microarrays 100. The multiplexed microarray cassette 1300 includes a base 1302 and some embodiments may also include a cover 1304 that is coupleable to the base 1302 to apply downward pressure to the multiplexed microarrays 100 therein as discussed in more detail below. However, in other embodiments, the cover 1304 may be omitted (e.g., in embodiments in which a sealing film is used to seal the microarrays 110).

Figure 17:
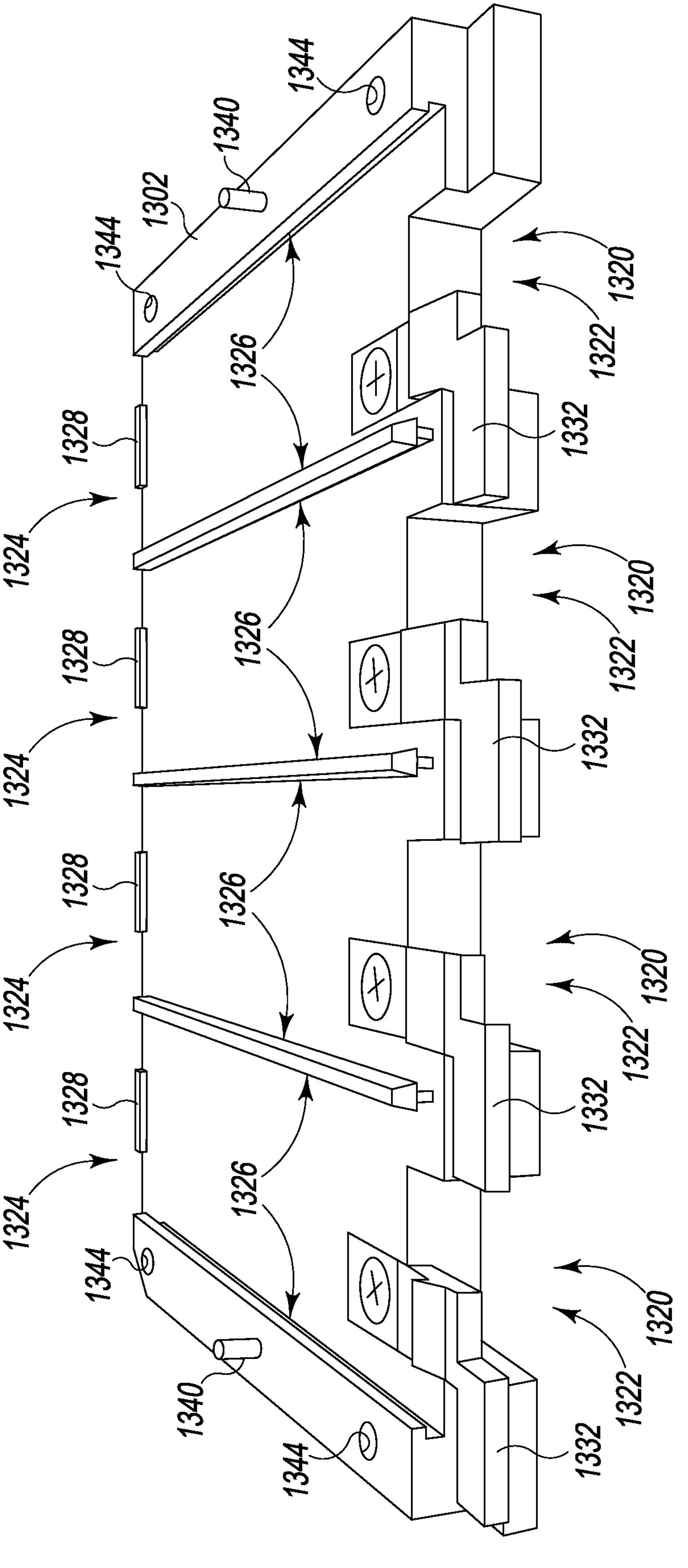
FIG. 17 is a side perspective view of a base of the multiplexed microarray cassette of FIG. 16.

The illustrative base 1302 includes four array tracks 1320 that are shaped and sized to receive the multiplexed microarrays 100. However, in other embodiments, the base 1304 may include additional or fewer tracks 1320. As shown in FIG. 17, each track 1320 includes a loading end 1322 at which the respective multiplexed microarray 100 may be inserted into the track 1320 and a back end 1324. Each track 1320 also includes a pair of lateral slots 1326 that extend longitudinally down the track 1320. The lateral slots 1326 are sized to receive the substrate 102 of the respective multiplexed microarray 100. To load the multiplexed microarray 100 in the track 1320, the longitudinal ends of the substrate 102 of the multiplexed microarray 100 may be positioned into the lateral slots 1326, and the multiplexed microarray 100 may be slid into place. Each track 1320 also includes a stop 1328 to restrict or otherwise prevent the multiplexed microarray 100 from sliding out of the track 1320 from the back end 1324.

Illustratively, the stops 1328 are embodied as individual lips that extend upwardly from a bottom surface 1310 of the track at the back end 1324.

Each track 1320 also includes a latch 1332 located at the loading end 1322 of the track 1320. Each latch 1332 is movable from a locked position to an unlocked position. When in the locked position, the latch 1332 restricts or prevents the respective multiplexed microarray 100 from sliding out of the track 1320 from the loading end 1322. The multiplexed microarray 100 may be loaded into or slid out of the track 1320 by moving the respective latch 1332 to the unlocked position. Illustratively, the latch 1332 is formed from a resilient material, such as a plastic material, that causes the latch 1332 to return to the locked position from the unlocked position when released.

In embodiments in which the cover 1304 is used, the base 1302 may also include a pair of pins 1340 extending upwardly from a top surface 1312 of the base 1302. The pins 1340 are positioned and sized to be received in corresponding pin apertures 1342 defined in the cover 1304. Additionally, the base 1302 may include a plurality of threaded apertures 1344 configured to receive corresponding threaded bolts or screws 1346 of the cover 1304 to secure the cover 1304 to the base 1302. However, in other embodiments, other securing devices or techniques may be used to secure the cover 1304 to the base 1302.

Figure 18:
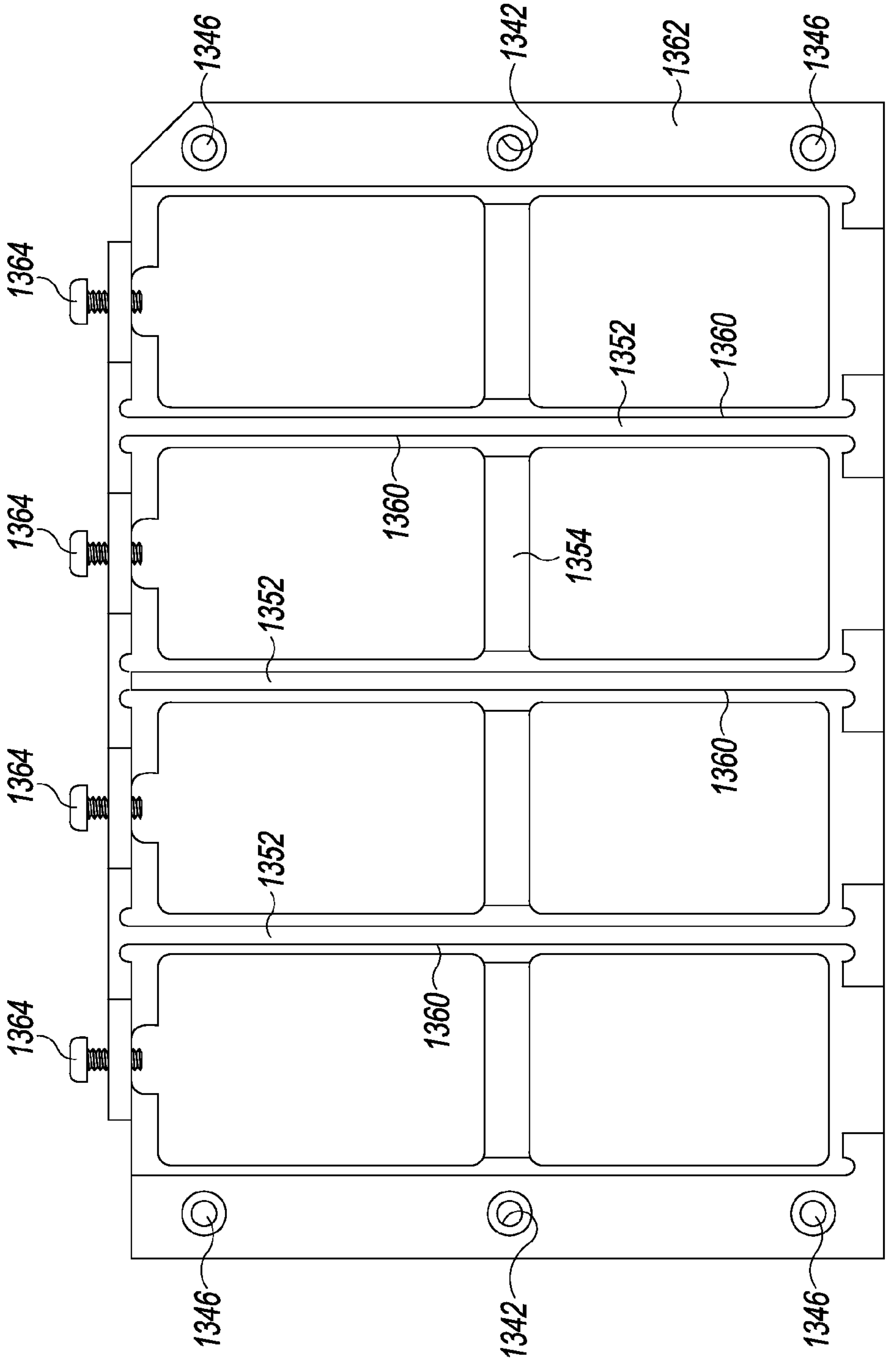
FIG. 18 is a plan view of a bottom surface of a cover of the multiplexed microarray cassette of FIG. 16.

The illustrative cover 1304 includes a window 1350 through which loaded multiplexed microarrays 100 may be viewed when the cover 1304 is secured to the base 1302. However, in other embodiments, the window 1350 may be omitted. The window 1350 includes a plurality of lateral crossbars 1352 and a longitudinal crossbar 1354 to provide an amount of rigidity and strength to the cover 1304, which is used to exert a downward sealing pressure. As illustrated in FIG. 18, the cover 1304 also includes a plurality of recesses 1360 defined on a lower surface 1362. Each recess 1360 is sized and positioned to receive an upper portion of a respective covering device (e.g., a rigid coverplate such as a glass slide, a compressible coverplate or other compressible sealing material, etc.) that aligns to the top surface of the multiplex microarray assembly when the multiplexed microarray 100 is loaded in the tracks 1320 and the cover 1304 is secured to the base 1302. The cover 1304 also includes a plurality of locking bolts, screws, or spring plungers 1364 located at an end 1366 of each recess 1360. The screws 1364 are usable to further secure the covering devices in the multiplexed microarray cassette 1300 when the cover 1304 is coupled to the base 1302.

Figure 19:
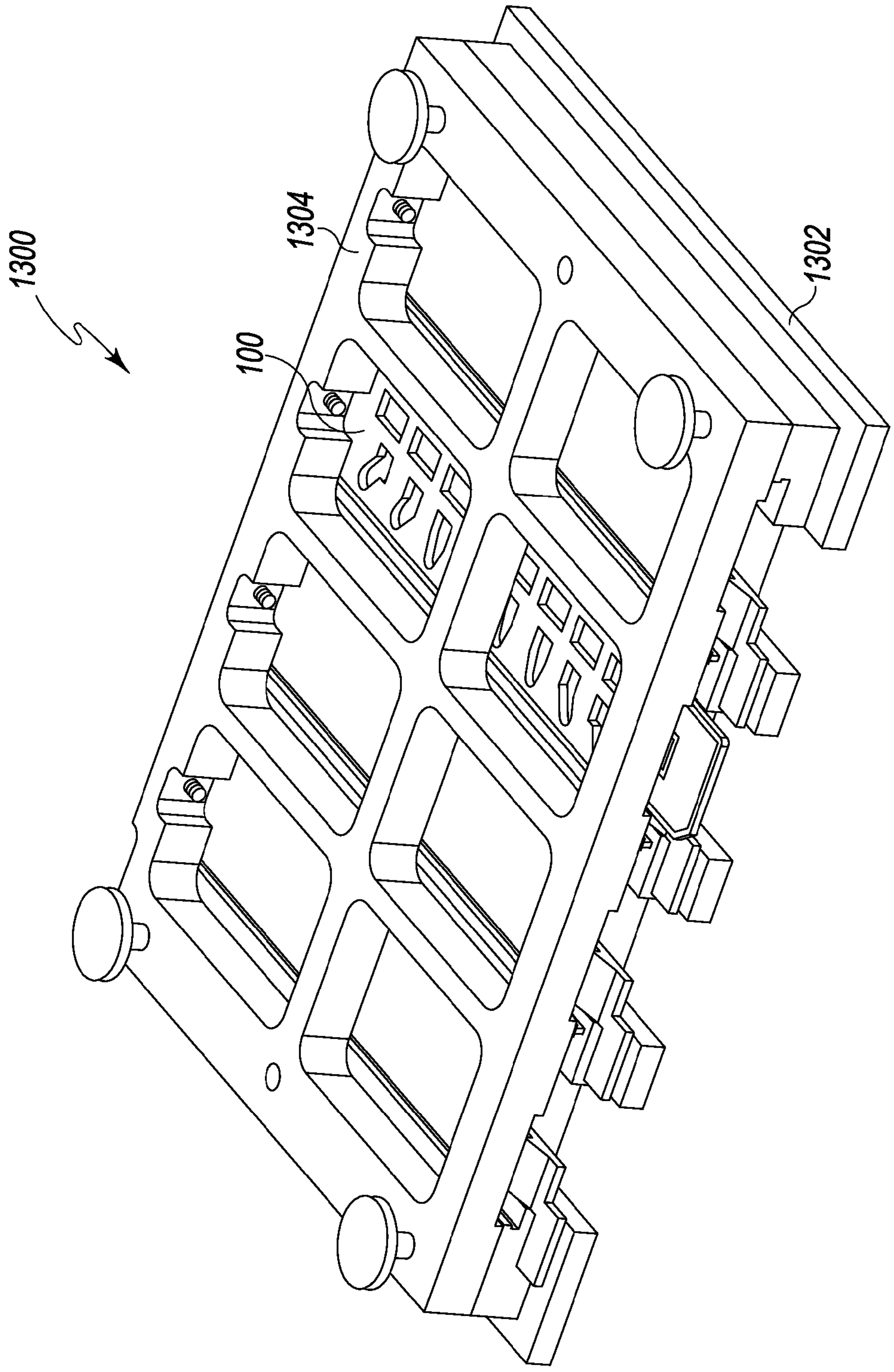
FIG. 19 is a perspective view of the multiplexed microarray cassette of FIG. 16 in an assembled configuration having a plurality of microarrays received therein.
Figure 20:
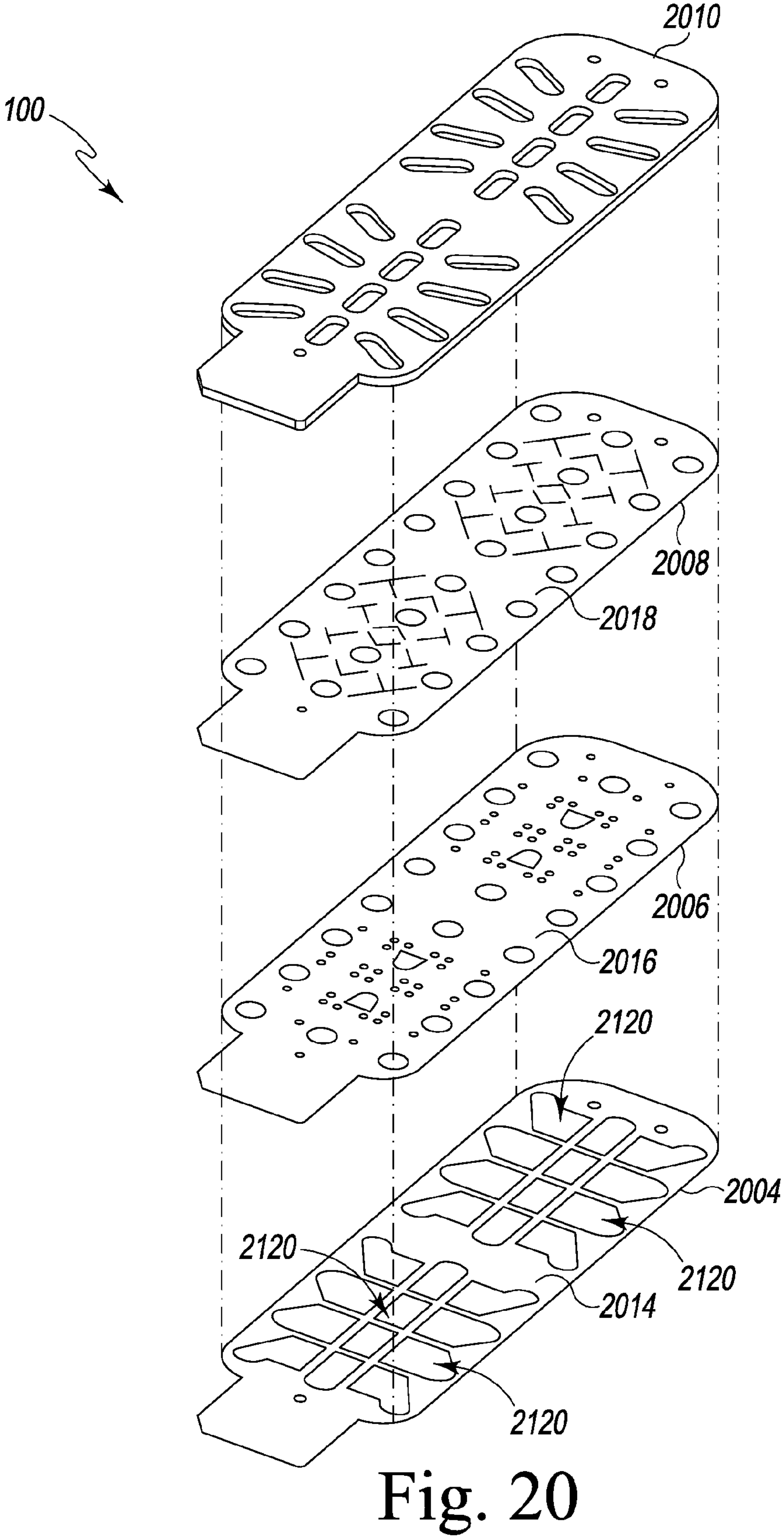
FIG. 20 is an exploded perspective view of another embodiment of a multiplexed microarray.

As shown in FIG. 19, after the multiplexed microarrays 100 are loaded into the tracks 1320 and the cover 1304 is secured to the base 1302, the multiplexed microarray cassette 1300 may be used to perform multiple assays at a time. In some embodiments, the multiplexed microarrays 100 may be loaded into the cassette 1300 prior to application of the analyte. Once loaded in the multiplexed microarray cassette 1300, the multiplexed microarrays 100 may be used with standard automated pipette machines to deposit the samples therein. Alternatively, the analyte may be deposited in the multiplexed microarrays 100 prior to loading the multiplexed microarrays 100 into the cassette 1300. Additionally, in some embodiments, a single cover or covering device may be used to cover each of the multiplexed microarrays 100 in place of individual covering devices. For example, in some embodiments, the cover 1304 is not used and a sealing film or foil similar to sealing film 660 may be used. The sealing film or foil is adhered to the top surfaces of the individual multiplexed microarrays to form a pneumatic seal to the individual chambers/wells. Attachment of the sealing film or foil may be accomplished via an appropriate adhesive or via a heatseal operation.

Another embodiment of a multiplexed microarray 100 that includes multiple layers of various chamber/channel geometry is illustrated in FIGS. 20-24. In that embodiment, the multiplexed microarray 100 includes the substrate 102 (not shown in FIG. 20), a chamber layer 2004, a lower channel layer 2006, an upper channel layer 2008, and a port layer 2010. The chamber layer 2004 is coupled or otherwise attached to the upper surface 112 of the substrate 102. Similarly, the lower channel layer 2006 is coupled to or otherwise attached to an upper surface 2014 of the chamber layer 2004. The upper channel layer 2008 is coupled or otherwise attached to an upper surface 2016 of the lower channel layer 2006, and the port layer 2010 is coupled or otherwise attached to an upper surface 2018 of the upper channel layer 2008.

Figure 21:
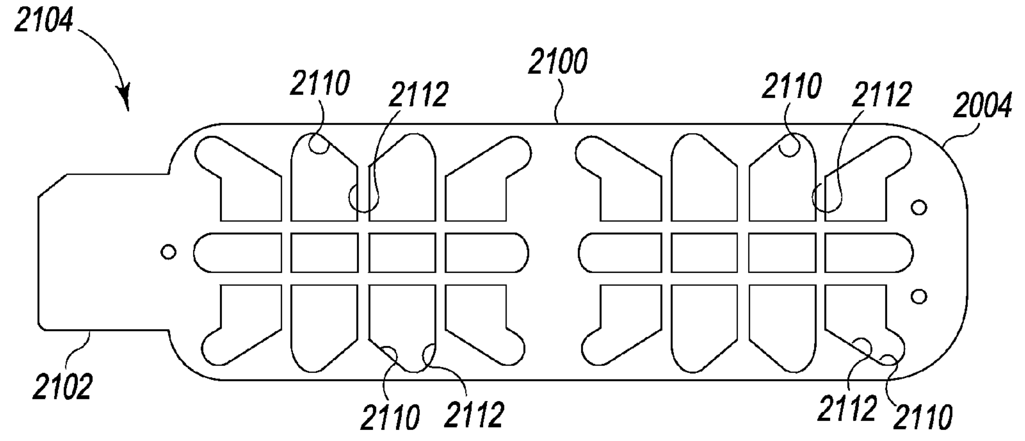
FIG. 21 is a plan view of one embodiment of a chamber layer of the multiplexed microarray of FIG. 20.

Similar to the chamber layer 104, the chamber layer 2004 may be formed from any suitable hydrophobic material including a plastic material such as polyethylene terephthalate (PET), an elastomer such as silicone, polyurethane, or latex, or other hydrophobic material. As illustrated in FIG. 21. The chamber layer 2004 includes an elongated body 2100 and a tab 2102 extending from an end 2204 of the elongated body 2100. The elongated body 2100 is sized to cover the upper surface 112 of the substrate 102 when coupled thereto. The chamber layer 2004 also includes a plurality of elongated apertures 2110 defined therethough. The apertures 2110 are respectively defined by corresponding inner sidewalls 2112 of the chamber layer 2104. The apertures 2110 are located on the chamber layer 2104 in a position such that, when the chamber layer 2104 is coupled to the substrate 102, each one of the microarrays 120 formed on the substrate 102 is positioned in a corresponding aperture 2110. That is, each microarray 120 is laterally surrounded by one of the sidewalls 2112 of the chamber layer 704 that defines the corresponding aperture 2110 to form a microarray chamber 2120 (see FIG. 20). Each microarray chamber 2120 has a substantially equal lateral cross-sectional area such that identical volumes of analyte fill each microarray chamber 2120 to substantially the same height.

Figure 22:
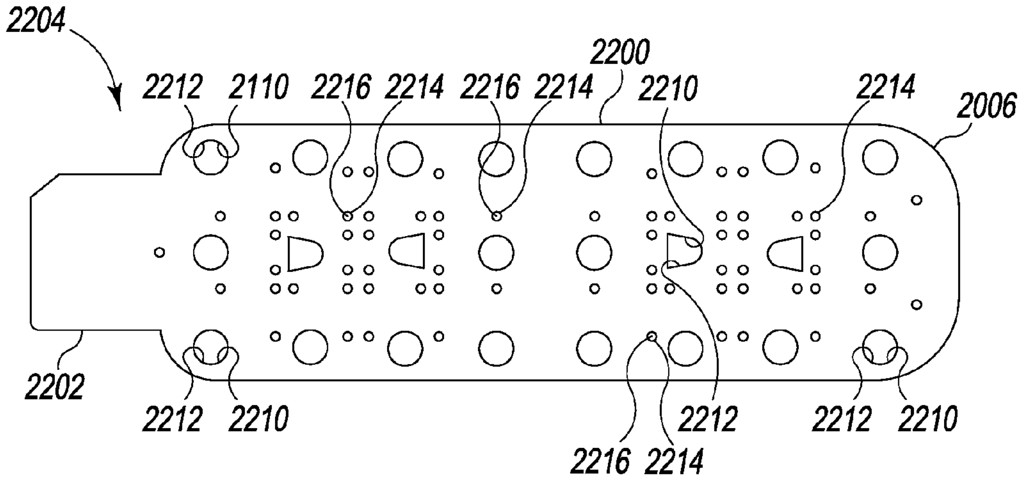
FIG. 22 is a plan view of one embodiment of a channel layer of the multiplexed microarray of FIG. 20.

Referring now to FIG. 22, the lower channel layer 2006 provides a fluid channel between the upper channel layer 2008 and the chamber layer 2004. In the illustrative embodiment, the lower channel layer 2006 is relatively thin and formed from a plastic material. The lower channel layer 2006 includes an elongated body 2200 and a tab 2202 extending from an end 2204 of the elongated body 2200. The elongated body 2200 is sized to cover the upper surface 2014 of the chamber layer 2004 when coupled thereto.

The lower channel layer 2206 includes a plurality of fluid apertures or channels 2210 defined therethrough. The apertures 2210 are respectively defined by corresponding inner sidewalls 2212 of the channel layer 2006. The apertures or slits 2210 form vertical channels through the lower channel layer 2006 and are shaped and sized to allow flow of analyte when applied to the multiplexed microarray 100. In the illustrative embodiment, the apertures 2210 are embodied as circular or oval-like openings, but apertures having other shapes and sizes may be used in other embodiments. The apertures or slits 2210 are located in the lower channel layer 2006 such that apertures 2210 are superimposed over the apertures 2110 of the chamber layer 704 when attached or otherwise coupled thereto.

The lower channel layer 2006 also includes a plurality of vent apertures or channels 2214 defined therethrough. The vent apertures 2214 form vertical channels through the lower channel layer and are sized and shaped to allow flow of air from the microarray chamber 2120 during filling of the chamber 2120 with an analyte. The vent aperture 2214 are respectively defined by corresponding inner sidewalls 2216. Illustratively, the vent apertures 2214 are embodied as circular openings but may have other shapes in other embodiments. The vent apertures 2214 are located on the lower channel layer 2206 such that, when the lower channel layer 2006 is coupled to the chamber layer 2004, each vent apertures 2214 is superimposed over a corresponding aperture 2110. In the illustrative embodiment, the lower channel layer 2006 includes a greater number of vent apertures 2214 than the number of apertures 2110 defined through the chamber layer 2004. As such, two or more vent apertures 2214 are superimposed over each aperture 2110 of the chamber layer 2004 when the lower channel layer 2006 is coupled thereto to allow air to flow out of each associated microarray chamber 2120.

Figure 23:
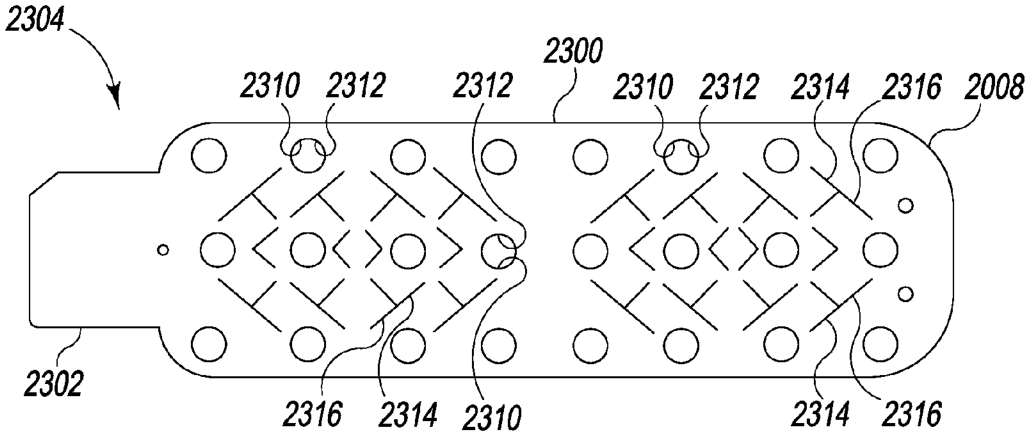
FIG. 23 is a plan view of one embodiment of another channel layer of the multiplexed microarray of FIG. 20.

Referring now to FIG. 23, the upper channel layer 2008 provides a fluid channel between the port layer 2010 and the lower channel layer 2006. The upper channel layer 2008 may be formed from any suitable plastic material that may be adhered to the port layer 2010. In one particular embodiment, the upper channel layer 2008 is formed from a polymer material. The upper channel layer 2008 includes an elongated body 2300 and a tab 2302 extending from an end 2304 of the elongated body 2300. The elongated body 2300 is sized to cover the upper surface 2016 of the lower channel layer 2006 when coupled thereto.

The upper channel layer 2008 also includes a plurality of fluid apertures or channels 2310 and a plurality of vent apertures or channels 2314. The fluid apertures 2310 form vertical channels through the upper channel layer 2008 and are shaped and sized to allow flow of an analyte when applied to the multiplexed microarray 100. The fluid apertures 2310 are respectively defined by corresponding inner sidewalls 2312. Illustratively, the fluid apertures 2310 are embodied as circular or oval-like apertures, but apertures having other shapes and sizes may be used in other embodiments. Similarly, the vent apertures 2314 form vertical channels through the upper channel layer 2008 and are shaped and sized to allow airflow from the microarray chamber 2120 when an analyte is applied to the multiplexed microarray 100. The vent apertures 2314 are respectively defined by corresponding inner sidewalls 2316 and embodied as elongated slits or openings having one or more branches. For example, some of the vent apertures 2314 have a substantially "T" shape. Of course, vent apertures having other shapes and sizes may be used in other embodiments.

When the upper channel layer 2008 is coupled to the lower channel layer 2006, the fluid apertures 2310 are superimposed over the fluid apertures 2210 of the lower channel layer 2006 and the vent apertures 2314 are superimposed over the vent apertures 2214 of the lower channel layer 2006. In particular, each vent aperture 2314 may be superimposed over one or more of the vent apertures 2214, which are located above each microarray chamber 2120. As such, the fluid apertures 2210, 2310 form a fluid channel to the associated microarray chamber 2120 and the vent apertures 2214, 2314 form a vent channel to allow air to flow out of the associated microarray chamber 2120 during filling of the chamber 2120 with analyte.

Figure 24:
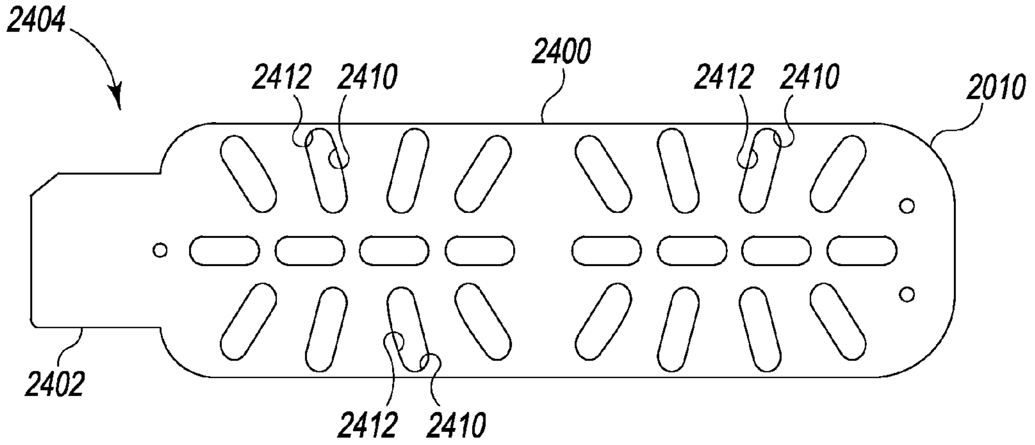
FIG. 24 is a plan view of one embodiment of a port layer of the multiplexed microarray of FIG. 20.

Referring now to FIG. 24, the port layer 2010 is coupled to the upper surface 2018 of the upper channel layer 2008. The port layer 2010 may be formed from any suitable material capable of forming a seal with the upper channel layer 2008. In the illustrative embodiment, the port layer 2010 is formed from a compressible material but may be formed from other materials in other embodiments. The port layer 2010 includes an elongated body 2400 and a tab 2402 extending from an end 2404 of the elongated body 2400. The elongated body 2400 is sized to cover the upper surface 2018 of the upper channel layer 2008 when couple thereto.

The port layer 2010 includes a plurality of fill ports 2410 defined therethrough. The fill ports 2410 form vertical channels through the port layer 2010 and are sized and shaped to allow flow of an analyte to the microarray chamber 2020 as discussed below. The fill ports 2410 are respectively defined by corresponding inner sidewalls 2412. Illustratively, the fill ports 2410 are embodied as elongated oval openings but may have other shapes in other embodiments. The fill ports 2410 are located on the port layer 2010 such that, when the port layer 2010 is coupled to the upper channel layer 2008, each fill port 2410 is superimposed over a corresponding fluid aperture or channel 2310 and one or more vent apertures or channels 2314 of the upper channel layer 2008. Additionally, it should be appreciated that, in the illustrative embodiment, the fill ports 2410 are located or otherwise defined in the port layer 2010 according to the pipette distance of standard automated pipette machines similar to the port layer 106 described above in regard to FIG. 5.

As described above, the multiplexed microarray 100 of FIGS. 20-24 includes multiple channel layers 2006, 2008 located between the chamber layer 2004 and the port layer 2010. However, in other embodiments additional or fewer channel layers may be used. For example, in some embodiments, the channel layer 2006 may be omitted from the multiplexed microarray 100. In such embodiments, the channel layer 2008 is coupled directly to the upper surface 2014 of the chamber layer 2004. Additionally, in other embodiments, channel layers having other channel geometry may be used to facilitate the loading of analyte into the microarray chamber 2120 and movement of air out of the wells. Additionally, it should be appreciated that a cover may be used with the multiplexed microarray 100 of FIGS. 20-24. The cover may be embodied as a coverplate, such as compressible coverplate 650 of FIG. 7, or a sealing film or foil, such as sealing film 660 of FIG. 8. Additionally, as described above, the sealing film or foil may be sized to over multiple multiplexed microarrays 100 in some embodiments.

There is a plurality of advantages of the present disclosure arising from the various features of the apparatuses, circuits, and methods described herein. It will be noted that alternative embodiments of the apparatuses, circuits, and methods of the present disclosure may not include all of the features described yet still benefit from at least some of the advantages of such features. Those of ordinary skill in the art may readily devise their own implementations of the apparatuses, circuits, and methods that incorporate one or more of the features of the present disclosure and fall within the spirit and scope of the present invention as defined by the appended claims.

The invention claimed is:

1. A multiplexed microarray comprising:
   - a substrate having a plurality of microarrays formed on an upper surface of the substrate;
   - a chamber layer attached to the upper surface of the substrate, the chamber layer having a plurality of apertures formed therethrough, the plurality of apertures and the upper surface of the substrate cooperating to form a plurality of wells, each of the wells having a corresponding microarray of the plurality of microarrays located therein;
   - a first channel layer disposed on the chamber layer, the first channel layer having a plurality of first fluid channels, each of the first fluid channels being superimposed over a corresponding aperture of the plurality of apertures of the chamber layer; and a port layer coupled to an upper surface of the first channel layer, the port layer having a plurality of fill ports formed therethrough, each of the fill ports being superimposed over a corresponding first fluid channel of the plurality of first fluid channels of the first channel layer such that each of the fill ports is in fluid communication with a corresponding well of the plurality of wells of the chamber layer through the corresponding first fluid channel of the plurality of first fluid channels of the first channel layer, wherein each fluid channel of the plurality of first fluid channels comprises an elongated slit and an opening fluidically coupled to a lateral end of the elongated slit, the opening having a width greater than the width of the elongated slit, and wherein each of the fill ports of the port layer is superimposed over an opening of the corresponding first fluid channel.

2. The multiplexed microarray of claim 1, wherein each fluid channel of the plurality of first fluid channels comprises a substantially circular opening, and wherein the first channel layer further comprises a plurality of vent apertures and each of the fill ports of the port layer is superimposed over at least a portion of a corresponding vent aperture of the plurality of vent apertures of the first channel layer.

3. The multiplexed microarray of claim 2 further comprising a second channel layer attached to the upper surface of the chamber layer, the second channel layer having a plurality of second fluid channels and a plurality of vent apertures, each of the plurality of second fluid channels and each of the plurality of vent apertures being superimposed over a corresponding well of the plurality of wells of the chamber layer, wherein the first channel layer is attached to an upper surface of the second channel layer such that each of the first fluid channels is superimposed over a corresponding second fluid channel of the plurality of second fluid channels and wherein at least a portion of each of the vent apertures of the first channel layer is superimposed over a corresponding vent aperture of the plurality of the vent apertures of the second channel layer.

4. The multiplexed microarray of claim 1, wherein the port layer further includes a plurality of vent holes, each of the vent holes being superimposed over at least one of the plurality of first fluid channels of the first channel layer.

5. The multiplexed microarray of claim 1, wherein each microarray of the plurality of microarrays is spaced apart from one or more of its adjacent microarrays of the plurality of microarrays in a distance less than 9 millimeters.

6. The multiplexed microarray of claim 5, wherein each of the fill ports of the port layer is spaced apart from one or more of its adjacent fill ports of the fill ports in a distance of about 9 millimeters.

7. The multiplexed microarray of claim 1, wherein the substrate comprises a substrate having twenty-four microarrays formed on its upper surface, each of the twenty-four microarrays being spaced apart from one or more of its adjacent microarrays of the twenty-four microarrays in a distance less than 9 millimeters.

8. The multiplexed microarray of claim 1, wherein the plan view, cross-sectional area of each well of the plurality of wells is substantially equal.

9. The multiplexed microarray of claim 1, wherein the first channel layer is compressible.

10. The multiplexed microarray of claim 1, wherein the substrate comprises a substrate having at least eight microarrays formed on its upper surface.

11. The multiplexed microarray of claim 1, wherein the chamber layer is formed from one of a hydrophobic plastic material and an elastomer material.

12. The multiplexed microarray of claim 1 wherein the port layer is a compressible port layer, and wherein the port layer is formed from a polymer material.

13. The multiplexed microarray of claim 12, further comprising a coverplate coupled to an upper surface of the compressible port layer, the coverplate and the port layer cooperating to pneumatically seal a plurality of elongated wells, wherein each of the elongated wells is formed by a sidewall of the port layer, the sidewalls of the chamber layer, and the upper surface of the substrate.

14. The multiplexed microarray of claim 1, further comprising a coverplate coupled to an upper surface of the port layer, the coverplate including a sealing gasket cooperating with the upper surface of the port layer to pneumatically seal a plurality of elongated wells, wherein each of the elongated wells is formed by a sidewall of the port layer, the sidewalls of the chamber layer, and the upper surface of the substrate.

15. The multiplexed microarray of claim 1, further comprising a sealing film coupled to an upper surface of the port layer, the sealing film and the port layer cooperating pneumatically seal a plurality of elongated wells, wherein each of the elongated wells is formed by a sidewall of the port layer, the sidewalls of the chamber layer, and the upper surface of the substrate.

16. The multiplexed microarray of claim 1, wherein the plurality of wells comprises a plurality of first elongated wells located toward a first longitudinal side of the multiplexed microarray and a plurality of second elongated wells located toward a second longitudinal side of the multiplexed microarray, and further comprising a plurality of third elongated wells centrally located between the plurality of first elongated wells and the plurality of second elongated wells, each of the third elongated wells having a corresponding microarray of the plurality of microarrays located therein.

17. A multiplexed microarray comprising:

a substrate having a plurality of microarrays formed on an upper surface of the substrate;

a chamber layer attached to the upper surface of the substrate, the chamber layer having a plurality of apertures formed therethrough, the plurality of apertures and the upper surface of the substrate cooperating to form a plurality of wells, each of the wells having a corresponding microarray of the plurality of microarrays located therein;

a first channel layer disposed above the chamber layer, the first channel layer having a plurality of first fluid channels, each of the first fluid channels being superimposed over a corresponding aperture of the plurality of apertures of the chamber layer; and a port layer coupled to an upper surface of the first channel layer, the port layer having a plurality of fill ports formed therethrough, each of the fill ports being superimposed over a corresponding first fluid channel of the plurality of first fluid channels of the first channel layer such that each of the fill ports is in fluid communication with a corresponding well of the plurality of wells of the chamber layer through the corresponding first fluid channel of the plurality of first fluid channels of the first channel layer;

a second channel layer attached to the upper surface of the chamber layer, the second channel layer having a plurality of second fluid channels, at least a portion of each of the second fluid channels being superimposed over a corresponding well of the plurality of wells of the chamber layer, wherein the first channel layer is attached to an upper surface of the second channel layer such that each of the first fluid channels are superimposed over a second fluid channel of the second fluid channels of the second channel layer.

18. The multiplexed microarray of claim 17, wherein each fluid channel of the plurality of second fluid channels comprises an elongated slit.

19. The multiplexed microarray of claim 17, wherein the port layer further includes a plurality of vent holes, each of the vent taste holes being superimposed over at least one of the plurality of first fluid channels of the first channel layer.

20. The multiplexed microarray of claim 17, wherein each microarray of the plurality of microarrays is spaced apart from one or more of its adjacent microarrays of the plurality of microarrays in a distance less than 9 millimeters.

21. The multiplexed microarray of claim 20, wherein each of the fill ports of the port layer is spaced apart from one or more of its adjacent fill ports of the fill ports in a distance of about 9 millimeters.

22. The multiplexed microarray of claim 17, wherein the substrate comprises a substrate having twenty-four microarrays formed on its upper surface, each of the twenty-four microarrays being spaced apart from one or more of its adjacent microarrays of the twenty-four microarrays in a distance less than 9 millimeters.

23. The multiplexed microarray of claim 17, wherein the plan view, cross-sectional area of each well of the plurality of wells is substantially equal.

24. The multiplexed microarray of claim 17, wherein the first channel layer is compressible.

25. The multiplexed microarray of claim 17, wherein the substrate comprises a substrate having at least eight microarrays formed on its upper surface.

26. The multiplexed microarray of claim 17, wherein the chamber layer is formed from one of a hydrophobic plastic material and an elastomer material.

27. The multiplexed microarray of claim 17 wherein the port layer is a compressible port layer, and wherein the port layer is formed from a polymer material.

28. The multiplexed microarray of claim 27, further comprising a coverplate coupled to an upper surface of the compressible port layer, the coverplate and the port layer cooperating to pneumatically seal a plurality of elongated wells, wherein each of the elongated wells is formed by a sidewall of the port layer, the sidewalls of the chamber layer, and the upper surface of the substrate.

29. The multiplexed microarray of claim 17, further comprising a coverplate coupled to an upper surface of the port layer, the coverplate including a sealing gasket cooperating with the upper surface of the port layer to pneumatically seal a plurality of elongated wells, wherein each of the elongated wells is formed by a sidewall of the port layer, the sidewalls of the chamber layer, and the upper surface of the substrate.

30. The multiplexed microarray of claim 17, further comprising a sealing film coupled to an upper surface of the port layer, the sealing film and the port layer cooperating pneumatically seal a plurality of elongated wells, wherein each of the elongated wells is formed by a sidewall of the port layer, the sidewalls of the chamber layer, and the upper surface of the substrate.

31. The multiplexed microarray of claim 17, wherein the plurality of wells comprises a plurality of first elongated wells located toward a first longitudinal side of the multiplexed microarray and a plurality of second elongated wells located toward a second longitudinal side of the multiplexed microarray, and further comprising a plurality of third elongated wells centrally located between the plurality of first elongated wells and the plurality of second elongated wells, each of the third elongated wells having a corresponding microarray of the plurality of microarrays located therein.

* * * * *